US009989539B2

(12) United States Patent
Ramirez et al.

(10) Patent No.: US 9,989,539 B2
(45) Date of Patent: Jun. 5, 2018

(54) METHOD FOR DETECTING INJURY TO THE BRAIN

(71) Applicant: TEMPLE UNIVERSITY—OF THE COMMONWEALTH SYSTEM OF HIGHER EDUCATION, Philadelphia, PA (US)

(72) Inventors: Servio H. Ramirez, North Wales, PA (US); Slava Rom, Jenkintown, PA (US); Yuri Persidsky, North Wales, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days. days.

(21) Appl. No.: 14/406,400

(22) PCT Filed: Jun. 25, 2013

(86) PCT No.: PCT/US2013/047470
§ 371 (c)(1),
(2) Date: Dec. 8, 2014

(87) PCT Pub. No.: WO2014/004424
PCT Pub. Date: Jan. 3, 2014

(65) Prior Publication Data
US 2015/0140127 A1 May 21, 2015

Related U.S. Application Data

(60) Provisional application No. 61/664,352, filed on Jun. 26, 2012.

(51) Int. Cl.
*A01N 59/04* (2006.01)
*A61K 33/14* (2006.01)
*G01N 33/53* (2006.01)
*G01N 33/542* (2006.01)
*G01N 33/567* (2006.01)
*G01N 33/68* (2006.01)
*A61M 27/00* (2006.01)
*G01N 33/573* (2006.01)

(52) U.S. Cl.
CPC ....... *G01N 33/6896* (2013.01); *A61M 27/006* (2013.01); *G01N 33/573* (2013.01); *G01N 33/6872* (2013.01); *A61M 2210/0693* (2013.01); *G01N 2333/28* (2013.01); *G01N 2333/70596* (2013.01); *G01N 2333/91017* (2013.01); *G01N 2800/2871* (2013.01); *G01N 2800/56* (2013.01)

(58) Field of Classification Search
None
See application file for complete search history.

(56) References Cited

U.S. PATENT DOCUMENTS

| 2005/0203013 A1 | 9/2005 | Soker et al. |
| 2006/0116423 A1 | 6/2006 | Dash |
| 2008/0025959 A1 | 1/2008 | Daneman et al. |
| 2010/0178347 A1 | 7/2010 | Bullock et al. |
| 2010/0286586 A1 | 11/2010 | Odland |
| 2011/0053157 A1 | 3/2011 | Skog et al. |
| 2012/0015395 A1 | 1/2012 | Shusta et al. |

FOREIGN PATENT DOCUMENTS

| WO | 2004056386 A2 | 7/2004 |
| WO | 2004069870 A2 | 8/2004 |
| WO | 2004096160 A2 | 11/2004 |
| WO | 2010065968 A1 | 6/2010 |
| WO | 2011109440 A1 | 9/2011 |
| WO | 2012020307 A2 | 2/2012 |

OTHER PUBLICATIONS

Thompson et al, Clin. Vaccine Immunol., 2009, 16(5):765-71.*
Petty, et al., Junctional Complexes of the Blood-Brain Barrier: Permeability Changes in Neuroinflammation, Progress in Neurobiology 68 pp. 311-323 (2002).
Stamatovic, et al., Brain Endothelial Cell-Cell Junctions: How to "Open" the Blood Brain Barrier, Current Neuropharmacology, 6, pp. 179-192 (2008).
Bansal, et al., Traumatic Brain Injury and Intestinal Dysfunction: Uncovering the Neuro-Enteric Axis, Journal of Neurotrauma 26, pp. 1353-1359 (2009).
Zhao, et al., Enhancing Expression of Nrf2-Driven Genes Protects the Blood-Brain Barrier after Brain Injury, The Journal of Neuroscience, 27(38), pp. 10240-10248 (Sep. 19, 2007).
Abbott, et al., Astrocyte-Endothelial Interactions at the Blood-Brain Barrier, Nature Reviews/Neuroscience, vol. 7, pp. 41-53 (Jan. 2006).
Menascu, et al., Serum Biochemical Markers for Brain Damage in Children with Emphasis on Mild Head Injury, Pediatric Neurosurgery, 46, pp. 82-88 (2010).
Rom, Slava, et al., Tight Junction Complex Modification at the Blood-Brain Barrier in TBI, Journal of Neurotrauma, vol. 28 No. 6 140, Huguenot Street, 3rd Fl., New Rochelle, NY 10801 USA: Mary Ann Liebert Inc, (Jun. 2011).

(Continued)

*Primary Examiner* — Olga N Chernyshev
(74) *Attorney, Agent, or Firm* — Drinker Biddle & Reath LLP

(57) ABSTRACT

Provided is a method for detecting injury to the brain comprising: a) determining the level of a tight junction (TJ) protein in exosomes isolated from a test sample from a subject, wherein the TJ protein is occludin, claudin-3, claudin-5, claudin-12, ZO-1, ZO-2, ZO-3, JAM-A, JAM-B or JAM-C, or any combination thereof; b) comparing the level of the TJ protein in the test sample to the level of the TJ protein in a control sample, wherein an elevated level of the TJ protein in the test sample relative to the level of the TJ protein in the control sample indicates that the subject has an injury to the brain.

26 Claims, 24 Drawing Sheets

(56) References Cited

OTHER PUBLICATIONS

Stamatovic, et al., Relocalization of Junctional Adhesion Molecule A During Inflammatory Stimulation of Brain Endothelial Cells, Molecular and Cellular Biology, vol. 32, 17, pp. 3414-3427 (Jun. 2012).

International Search Report for PCT/US2013/047470 dated Nov. 29, 2013.

* cited by examiner

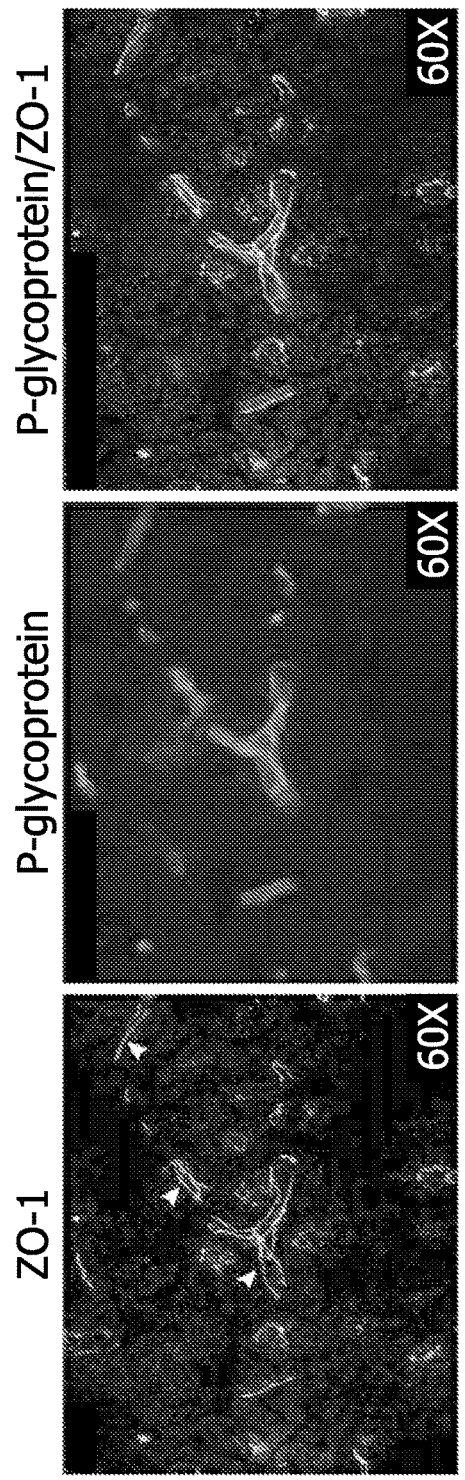

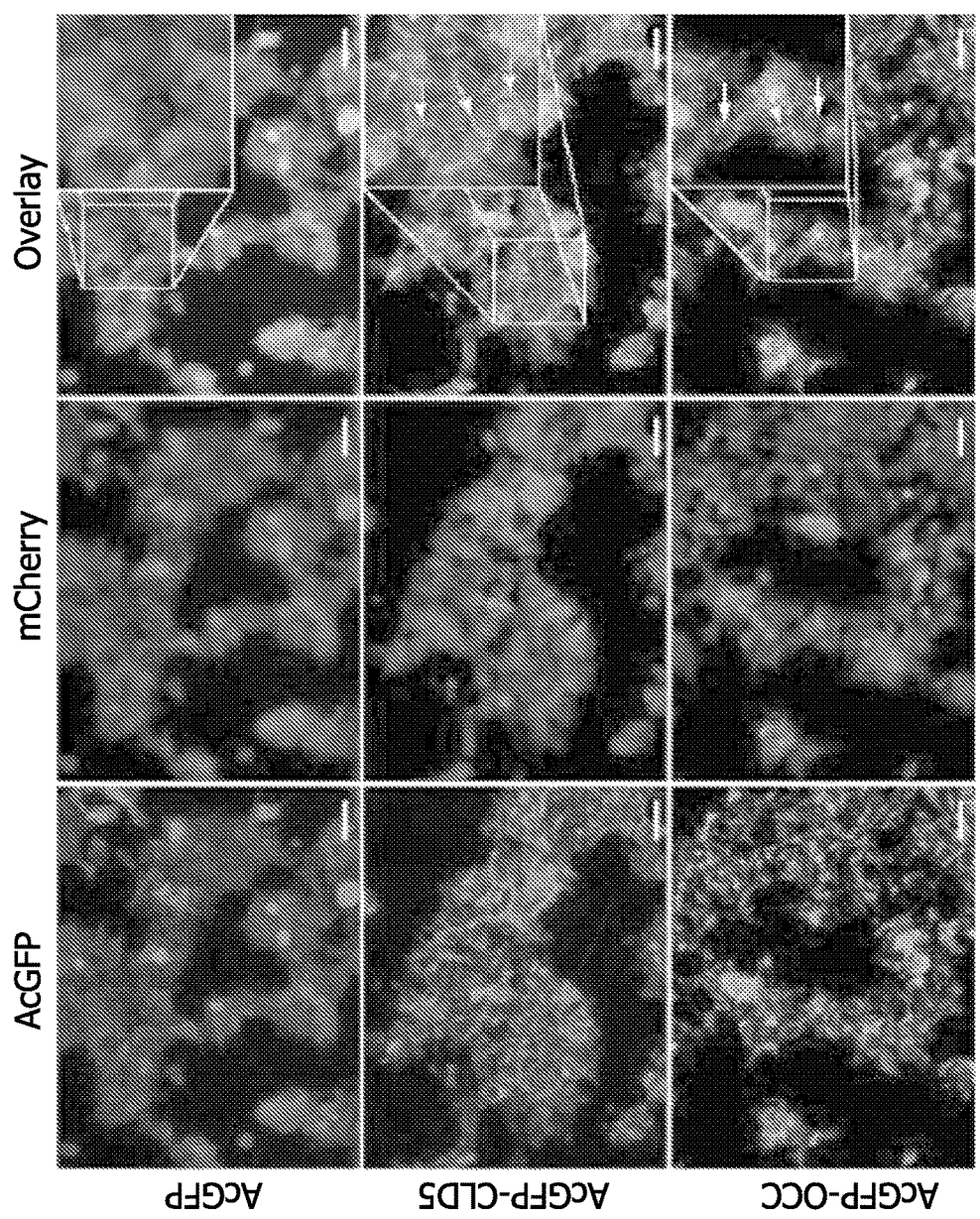

METHOD FOR DETECTING INJURY TO THE BRAIN

CROSS REFERENCE TO RELATED APPLICATION

This application claims benefit of U.S. Provisional Patent Application No. 61/664,352, filed Jun. 26, 2012, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Apr. 29, 2013, is named 35926_0452_00_WO_SL.txt and is 1,019 bytes in size.

FIELD OF THE INVENTION

The invention relates to a method for detecting injury to the brain.

BACKGROUND OF THE INVENTION

Traumatic brain injury (TBI) is considered to be a major health problem in the United States. Approximately every 16 seconds in the United States, a person suffers a TBI. The CDC estimates that 1.5 to 2 million individuals experience TBI annually, resulting in 1.4 million emergency department visits, 235,000 hospitalizations and 52,000 deaths. (Coronado V G, XU L, Basavaraju S V, McGuire L C, Wald M M, Faul M D, et al. Surveillance for traumatic brain injury-related deaths—United States, 1997-2007. *MMWR Surveill Summ.* 2011. 60(5):1-32). TBI is particularly devastating among young adults and children, making it the leading cause of death and disability in the United States. Almost half a million emergency department visits for TBI are made annually by children aged 0 to 14 years (Langlois J A, Rutland-Brown W, Walk M M. *J. Head Trauma Rehabil.* 2006. 21(5):357-8; Satz P, Zauch K, McCleary C, Light R, Asarnow R, Becker D. *Psychol Bull.* 1997: 122(2):107-31). In addition, according to a recent CDC report, Americans 65 and older experience a high rate of TBI due to the incidence of falls (Thomas K E, Stevens J A, Sarmiento K, Wald M M. 2005. *J. Safety Res.* 2008; 39(3):269-72). TBI also ranks at the top of common traumatic events involving the central nervous system (CNS), outpacing traumatic spinal cord injury by a factor of 10. The socioeconomic consequence of TBI can be quite significant; considering the injury costs associated with expenditures for acute treatment, long-term rehabilitation, and loss of productivity (Shi J, Xiang H, Wheeler K, Smith G A, Stallones L, Groner J, et al. *Brain inj.* 2009. 23(7):602-11). Despite TBI's major public health issues, resources allocated for TBI research (from basic science to clinical research) at the national level have not been met with the same level of urgency.
The Blood Brain Barrier (BBB)

The BBB is defined as the boundary that regulates access of blood components (influx of nutrients and efflux of waste) and immune cells into the brain (Abbott N J, Ronnback L, Hansson E. *Nat Rev Neurosci.* 2006. 7(1):41-53). Brain endothelial cells are connected by tight intercellular junctions (TJ) that provide the physical barrier characteristic of the BBB. Tight junction formation appears early in brain development greatly restricting the paracellular movement of solutes (water-soluble and polar compounds) and small ions into the brain (Anstrom J A, Thore C R, Moody D M, Brown W R. *Histochem Cell Biol.* 2007. 127(2):205-13). The BBB is conceptually part of a larger structure termed the neurovascular unit, which is composed of endothelial cells, glial cells, pericytes and neurons. Under physiological conditions, the role of the BBB is to protect and maintain the delicate neuronal environment. Disruption of the BBB leaves the CNS vulnerable to neuronal damage. In fact, BBB dysfunction is observed in virtually all aspects of neurodegeneration including: neurotrauma (stroke, head injury, hemorrhage), neuropathogenesis (viral, bacterial and parasitic), neurological disease (Alzheimer's disease, Multiple Sclerosis, Parkinson's disease), epilepsy and brain tumors (Persidsky Y, Ramirez S H, Haorah J, Kanmogne G D. *J Neuroimmune Pharmacol.* 2006. 1(3):223-36; Zlokovic B V. *Neuron.* 2008. 57(2):178-201; Oby E, Janigro D. *Epilepsia.* 2006. 47 (11): 1761-74).

Brain endothelial tight junction complexes at the molecular level are composed of the following proteins: occludin, claudin (claudin-3, 5, 12), Zonula Occludens protein (ZO-1, 2, 3), and the junctional adhesion molecules (JAM-A, B, C) (Abbott N J, Ronnback L, Hansson E. *Nat Rev Neurosci.* 2006. 7(1):41-53). The assembly of the tight junction is such that the intracellular ZO proteins form the major anchoring site for transmembranous occludin, claudin and JAM proteins to bind. In addition, via adaptor proteins the tight junction complex is bridged to the cytoskeleton of the cell. The tight junction complex is central to endothelial-endothelial adhesion and BBB integrity.
Injury to the BBB by Injury to the Brain Injury to the brain such as that sustained in TBI damages cerebral blood vessels which circumvents the barrier mechanisms of the BBB and thus allows blood contents to leak into the brain (Hicks R R, Baldwin S A, Scheff S W. *Mol Chem Neuropathol.* 1997. 32(1-3):1-16; Signoretti S, Vagnozzi R, Tavazzi B, Lazzarino G. *Neurosurg Focus.* 2010. 29(5):E1). Once leakage occurs, secondary events are triggered that contribute to further injury. At the end of the acute phase of TBI, leakage at the direct site of impact seals due to the natural clotting process. However, after a period of time the blood vessels in and around the lesion become more permeable than those in undamaged areas. This hyper-permeability leads to 1) a loss of control over the neurochemical environment around neurons and 2) entry of potentially toxic molecules into the CNS that exacerbates secondary damage (Hall E D, Bryant Y D, Cho W, Sullivan P G. *J Neurotrauma.* 2008. 25(3):235-47; Bazarian J J, Wong T, Harris M, Leahey N, Mookerjee S, Dombovy M. *Brain Inj.* 1999. 13(3):173-89).
Blast Mediated Brain Injury Blast induced neurotrauma (BINT) is a type of TBI that can occur when an individual is exposed to the blast wave of a detonated explosive. (Cernak, I and Noble-Haeusslein, L. J. *J Cereb Blood Flow Metab* 2010. 30:255-266). Because of the nature of modern warfare, military personnel engaged in conflict areas are at particular risk of experiencing a BINT event. (Cernak, I. *Front Neurol* 2010. 1:151). These injuries occur as a result of an impact by a shock wave with properties of increased pressure, heat and density. The damage is exacerbated by the prolonged negative pressure phase following immediately behind the shock wave front. Blast overexposure (BOP) generate acute damage to gas-filled organs (i.e. lungs) and solid organs. In the brain BINT causes distinct pathological changes as a direct result of the passing blast wave that accelerates and/or rotates the brain. (Pun, P B et al. *Front Neurol* 2011. 2:19). In addition, BOP causes enhanced vascular loading from the transfer of kinetic energy to the body's fluid phase (mainly the blood). Vascular loading causes oscillating fluidic waves that induce changes to the cerebrovasculature which lead to increase in BBB permeability, edema formation, vasospasms and altered blood flow. The neurological symptoms of BMBI range widely depending on the degree of injury and can manifest in months to years after exposure to the blast. (Svetlov S I, Prima V, Kirk D R, Gutierrez H, Curley K C, Hayes R L and Wang K K. *J. Trauma* 2010. 69:795-804).

Epilepsy and Seizures

Epilepsy is diagnosed when an individual experiences repeated convulsions over a given period of time. (Oby, E and Janigro D. *Epilepsia* 2006. 47:1761-1774). Not always involving convulsions, seizures are episodes of abnormal electrical activity in the brain which can manifest as changes in attention or behavior. Common causes of epilepsy include conginetal brain defects, infections, stroke, TBI, metabolic disorders and brain tumors. (van Vliet E A, et al. *Brain* 2007. 130: 521-534). A strong correlation exists between BBB disruption and seizures. Analysis of small molecular tracers that enter the brain when the BBB is disrupted has been shown in both humans and in animal studies of epilepsy. (van Vliet E A, et al. *Brain* 2007. 130: 521-534). Furthermore, abnormal electroencephalogram (EEG) patterns can be observed when there is hyper-permeability of the BBB. In fact serological studies in patients with epilepsy have shown the presence of neuronal and glial proteins (that normally are not present in the blood) as a consequence of BBB deregulation in epilepsy. While several methods can be used to determine directly the proper function of the BBB in animal models, a fitting (i.e., intravital microscopy, histology or analytical) technique for evaluating BBB integrity in humans does not exist.

Stroke

Stroke is the $4^{th}$ leading cause of death in the United States, affecting more than 750,000 individuals per year. (Ovbiagele B and Nguyen-Huynh M N. *Neurotherapeutics* 2011. 8:319-329). Stroke denotes a sudden disruption or stoppage of blood flow in the brain which subsequently deprives brain tissue of oxygen and nutrients. The interruption in blood flow can occur as a result of a blood clot blockage (ischemic stroke) or rupture (hemorrhagic stroke) of a cerebral blood vessel. (Lo E H, Dalkara T and Moskowitz M A. *Nat Rev Neurosci* 2003. 4:399-415). After the onset of stroke, edema formation develops and induces a rise in intracranial pressure which can lead to compression, herniation and damage of brain tissue. Increase in cerebrovascular permeability due to BBB disruption is a critical factor in the development of edema. (Jiang Q et al. *J. Cereb Blood Flow Metab* 2005. 25:583-592). Often the edema that forms worsens during the phase of reperfusion. Inflammatory mediators and cellular proteins from injured cells activate the endothelium and augments BBB permeability contributing not only to edema formation but to the disruption in neuronal homeostasis. (Cipolla M J, Huang Q and Sweet J G. *Stroke* 2011. 42:3252-3257).

Inflammatory and Infectious Diseases of the Brain

Many infectious diseases affecting the brain cause changes to the brain vasculature that often lead to a breach of the BBB. Examples of these types of diseases include viral infections caused by HIV-1, Rabies, cerebral malaria, and Japanese encephalitis virus. (Persidsky, Y et al. *J Immunol* 1997. 158:3499-3510; Fabis M J, Phares T W, Kean R B, Koprowski H and Hooper D C. *Proc Natl Acad Sci USA* 2008. 105:15511-15516; Tripathi A K, Sha W, Shulaev V, Stins M F and Sullivan D J, Jr. *Blood* 2009. 114: 4243-4252; Liu T H, Liang L C, Wang C C, Liu H C and Chen, W J. *J. Neurovirol* 2008. 14: 514-521). Also bacterial infections caused by *Escherichia coli* K1, group B *streptococcus, Listeria monocytogenes, Citrobacter freundii* and *Streptococcus pneumonia* strains have been shown to affect the BBB. (Huang S H, Stins M F and Kim K S. *Microbes Infect* 2000. 2:1237-1244). Under inflammatory conditions, the normal function of the BBB is compromised due to overproduction of pro-inflammatory molecules by inflammatory cells. Whether induced by trauma (i.e TBI), cerebrovascular accident (stroke), a pathogen or neurological disorder (i.e multiple sclerosis, Alzheimer's disease) the breach of the BBB is significantly driven by the up-regulation of inflammatory pathways in activated cells of the neurovascular unit and by the recruitment of immune cells. (Persidsky Y and Ramirez S H. In The Neurology of AIDS (Gendelman H E, Grant I, Everall I P, Lipton S A and Swindells S, eds) pp. 220-230. Oxford University Press, New York). BBB disruption is markedly enhanced by the recruitment of immune cells to the brain endothelium in a process that involves immune adhesion and transendothelial migration. Therefore BBB injury in neuroinflammation is believed to result from the disruption of junction complexes between brain microvascular endothelial cells that facilitates the diffusion of blood products and entry of leukocytes into the brain parenchyma.

Method for the Detection of Injury to the Brain

Until now most efforts on TBI serum biomarkers have centered on detecting neuronal and glial proteins that have leaked from the brain into the blood (Menascu S, Brezner A, Tschechmer S M, Rumeny P G. *Pediatr Neurosurg.* 2010. 46(2):82-8). Such candidate neuronal and glial proteins include: S100β, Tau, NSE (neuron-specific enolase), SBDPs (spectrin breakdown products), ApoE (apolipoprotein E) and GFAP (glial fibrillary acidic protein). Although there have been promising results, these candidate biomarkers have not proven entirely useful for the diagnosis of brain injury. All of these candidate biomarkers have been poor predictors of long-term outcome after TBI, some lacking specificity or sensitivity.

There remains a need for an objective, blood based diagnostic test and for an effective pharmacological (or biological) treatment for TBI, and other brain injuries.

SUMMARY OF THE INVENTION

Provided is a method for screening subjects for injury to the brain comprising:

a) determining the level of a tight junction (TJ) protein in exosomes from a test sample comprising blood, blood plasma, blood serum, cerebrospinal fluid or urine from a subject, wherein the TJ protein is occludin, claudin-3, claudin-5, claudin-12, ZO-1, ZO-2, ZO-3, JAM-A, JAM-B or JAM-C, or any combination thereof; and b) comparing the level of the TJ protein in the exosomes from the test sample to the level of the TJ protein in a control, wherein an elevated level of the TJ protein in the exosomes from the test sample relative to the level of the TJ protein in the control indicates that the subject has sustained an injury to the brain.

In some embodiments, the method for screening subjects for injury to the brain further comprises isolating exosomes from the test sample prior to determining the level of the TJ protein in the exosomes. In further embodiments, the level of the TJ protein is normalized by dividing it by the level of an exosome marker in the exosomes from the test sample and the level of the TJ protein in the control is normalized by dividing it by the level of an exosome marker in the control. In preferred embodiments, the exosome marker is CD63.

In some embodiments, the exosomes are isolated from the test sample by exosome precipitation or ultracentrifugation. In further embodiments, the exosomes are isolated from the test sample by binding to an agent that binds specifically to the TJ protein. In preferred embodiments, the agent that specifically binds to the TJ protein is an antibody or antibody fragment.

In some embodiments, the TJ protein is occludin or claudin-5. In further embodiments, the TJ protein is phosphorylated.

In some embodiments, the injury to the brain is traumatic brain injury (TBI), stroke, epilepsy, an inflammatory disease of the brain, Chronic Traumatic Encephalopathy (CTE) or Blast Induced Neurotrauma (BINT). In further embodiments, the control is a control sample obtained from a healthy normal subject, a control reference level, or a pooled control sample. In some embodiments, the blood comprises peripheral blood. In further embodiments, determining the level of the TJ protein is by enzyme-linked immunosorbent assay (ELISA), Western Blot analysis, immunoprecipitation, immunofluorescence assay, radioimmunoassay, chemiluminescence assay, flow cytometry, immunocytochemistry, or any combination thereof.

Provided is a method for determining whether an injury to the brain of a subject has progressed in severity, the method comprising:

a) determining the level of a TJ protein in exosomes from a first test sample comprising blood, blood plasma, blood serum, cerebrospinal fluid or urine from a subject at a first time point and from a second test sample second test sample comprising blood, blood plasma, blood serum, cerebrospinal fluid or urine from the subject at a second time point, wherein the TJ protein is occludin, claudin-3, claudin-5, claudin-12, ZO-1, ZO-2, ZO-3, JAM-A, JAM-B or JAM-C, or any combination thereof; and b) comparing the level of the TJ protein determined in exosomes from the first test sample to the level of the TJ protein in exosomes from the second test sample, wherein an elevated level of the TJ protein in exosomes from the second test sample relative to the level of the TJ protein in exosomes from the first test sample is an indication that the subject has an injury to the brain that has progressed.

In some embodiments, the method for determining whether an injury to the brain of a subject has progressed in severity further comprises isolating exosomes from the first test sample and a isolating exosomes from the second test sample prior to determining the level of the TJ protein in the exosomes. In further embodiments, the level of the TJ protein determined in exosomes from the first test sample is normalized by dividing it by the level of an exosome marker in the first test sample and the level of the TJ protein in exosomes from the second test sample is normalized by dividing it by the level of an exosome marker in the second test sample.

In some embodiments, the method further comprises:

a) determining the level of a non-TJ protein marker for injury to the brain in exosomes from the first and second test samples; and b) comparing the level of the non-TJ protein marker for injury to the brain determined in exosomes from the first test sample to the level of the protein marker for injury to the brain in exosomes from the second test sample, wherein an elevated level of the non-TJ protein marker for injury to the brain in exosomes from the second test sample relative to the level of the non-TJ protein marker for injury to the brain in exosomes from the first test sample is a further indication that the subject has an injury to the brain that has progressed in severity.

In some embodiments, the injury to the brain is traumatic brain injury (TBI), stroke, epilepsy, an inflammatory disease of the brain, Chronic Traumatic Encephalopathy (CTE) or Blast Induced Neurotrauma (BINT). In further embodiments, the blood comprises peripheral blood. In further embodiments, the exosomes are isolated from the first test sample and from the second test sample by exosome precipitation or ultracentrifugation. In yet further embodiments, determining the level of the TJ protein is by enzyme-linked immunosorbent assay (ELISA), Western Blot analysis, immunoprecipitation, immunofluorescence assay, radioimmunoassay, chemiluminescence assay, flow cytometry, immunocytochemistry, or any combination thereof.

Provided is a method for screening subjects for injury to the brain comprising:

a) selecting exosomes having a first tight junction (TJ) protein from a test sample comprising blood, blood plasma, blood serum, cerebrospinal fluid or urine from a subject, wherein the first TJ protein is occludin, claudin-5, claudin-12, ZO-2, ZO-3, JAM-A, JAM-B or JAM-C, or any combination thereof;

b) determining the level of a second tight junction (TJ) protein in the exosomes, wherein the TJ protein is occludin, claudin-3, claudin-5, claudin-12, ZO-1, ZO-2, ZO-3, JAM-A, JAM-B or JAM-C, or any combination thereof; and c) comparing the level of the second TJ protein in the exosomes from the test sample to the level of the second TJ protein in a control, wherein an elevated level of the second TJ protein in the exosomes from the test sample relative to the level of the second TJ protein in the control indicates that the subject has sustained an injury to the brain;

wherein the first and the second TJ protein may be the same TJ protein or may be a different TJ protein.

In some embodiments, the level of the TJ protein is normalized by dividing it by the level of an exosome marker in the exosomes from the test sample and the level of the TJ protein in the control is normalized by dividing it by the level of an exosome marker in the control. In preferred embodiments, the exosome marker is CD63.

In some embodiments, the exosomes are isolated from the test sample by exosome precipitation or ultracentrifugation. In further embodiments, the exosomes are isolated from the test sample by binding to an agent that binds specifically to the first TJ protein. In preferred embodiments, the agent that specifically binds to the first TJ protein is an antibody or antibody fragment.

In some embodiments, the second TJ protein is occludin or claudin-5. In further embodiments, the second TJ protein is phosphorylated.

In some embodiments, the injury to the brain is traumatic brain injury (TBI), stroke, epilepsy, an inflammatory disease of the brain, Chronic Traumatic Encephalopathy (CTE) or Blast Induced Neurotrauma (BINT). In further embodiments, the control is a control sample obtained from a healthy normal subject, a control reference level, or a pooled control sample. In yet further embodiments, the blood comprises peripheral blood. In yet further embodiments, the level of the TJ protein is by enzyme-linked immunosorbent assay (ELISA), Western Blot analysis, immunoprecipitation, immunofluorescence assay, radioimmunoassay, chemiluminescence assay, flow cytometry, immunocytochemistry, or any combination thereof.

Provided is a method for screening for subjects in which the injury to the brain has progressed, the method comprising:

a) isolating exosomes having a first TJ protein from a first test sample comprising blood, blood plasma, blood serum, cerebrospinal fluid or urine from a subject at a first time point and isolating exosomes from a second test sample comprising blood, blood plasma, blood serum, cerebrospinal fluid or urine from the subject at a second time point, wherein the first TJ protein is occludin, claudin-5, claudin-12, ZO-2, ZO-3, JAM-A, JAM-B or JAM-C, or any combination thereof;

b) determining the level of a second TJ protein in exosomes from the first and second test samples, wherein the second TJ protein is occludin, claudin-3, claudin-5, claudin-12, ZO-1, ZO-2, ZO-3, JAM-A, JAM-B or JAM-C, or any combination thereof, wherein the first and the second TJ protein may be the same TJ protein or may be a different TJ protein; and c) comparing the level of the second TJ protein determined in exosomes from the first test sample to the level of the second TJ protein in exosomes from the second test sample, wherein an elevated level of the second TJ protein in exosomes from the second test sample relative to the level of the second TJ protein in exosomes from the first test sample is an indication that the subject has an injury to the brain that has progressed.

In some embodiments, the level of the second TJ protein determined in exosomes from the first test sample is normalized by dividing it by the level of an exosome marker in the first test sample and the level of the second TJ protein in exosomes from the second test sample is normalized by dividing it by the level of an exosome marker in the second test sample.

In some embodiments, the method for screening for subjects in which the injury to the brain has progressed comprises:

a) determining the level of a non-TJ protein marker for injury to the brain in exosomes from the first and second test samples; and b) comparing the level of the non-TJ protein marker for injury to the brain determined in exosomes from the first test sample to the level of the non-TJ protein marker for injury to the brain in exosomes from the second test sample, wherein an elevated level of the non-TJ protein marker for injury to the brain in exosomes from the second test sample relative to the level of the non-TJ protein marker for injury to the brain in exosomes from the first test sample is a further indication that the subject has an injury to the brain that has progressed.

In some embodiments, the injury to the brain is traumatic brain injury (TBI), stroke, epilepsy, an inflammatory disease of the brain, Chronic Traumatic Encephalopathy (CTE) or Blast Induced Neurotrauma (BINT). In further embodiments, the blood comprises peripheral blood. In yet further embodiments, the exosomes are isolated from the first test sample and from the second test sample by exosome precipitation or ultracentrifugation. In some embodiments, determining the level of the TJ protein is by enzyme-linked immunosorbent assay (ELISA), Western Blot analysis, immunoprecipitation, immunofluorescence assay, radioimmunoassay, chemiluminescence assay, flow cytometry, immunocytochemistry, or any combination thereof. In further embodiments, determining the level of the non-TJ protein marker for injury to the brain is by enzyme-linked immunosorbent assay (ELISA), Western Blot analysis, immunoprecipitation, immunofluorescence assay, radioimmunoassay, chemiluminescence assay, flow cytometry, immunocytochemistry, or any combination thereof.

Provided is a method of isolating exosomes from a test sample comprising blood, blood plasma, blood serum, cerebrospinal fluid or urine from a subject comprising contacting the exosomes with an agent that binds a TJ protein, wherein the TJ protein is occludin, claudin-5, claudin-12, ZO-2, ZO-3, JAM-A, JAM-B or JAM-C, or any combination thereof.

Provided is a method comprising determining the level of a TJ protein in exosomes from a test sample comprising blood, blood plasma, blood serum, cerebrospinal fluid or urine from a subject, wherein the TJ protein is occludin, claudin-3, claudin-5, claudin-12, ZO-1, ZO-2, ZO-3, JAM-A, JAM-B or JAM-C, or any combination thereof; and comparing the level of the TJ protein in the exosomes from the test sample to the level of the TJ protein in a control, wherein an elevated level of the TJ protein in the exosomes from the test sample relative to the level of the TJ protein in the control indicates that the subject has sustained an injury to the brain; and conducting further diagnostic procedures on the subject related to the injury to the brain or treating a disorder or condition associated with the injury to the brain.

In some embodiments, the further diagnostic procedure comprises computed tomography (CT) scanning, magnetic resonance imaging (MRI), X-ray imaging, blood tests, physical examination, cognitive testing, electroencephalography, neuromonitoring, intracranial pressure (ICP) monitoring, assessing cerebral perfusion pressure (CPP) or determining the subject's Glasgow coma scale score (GCS). In further embodiments, the neuromonitoring comprises jugular venous oximetry, brain tissue oxygen tension monitoring, cerebral microdialysis or thermal diffusion flowmetry.

In some embodiments, the treatment comprises surgical treatment, head elevation, osmotic therapy, hyperventilation, debridement, optimizing venous drainage, cerebrospinal fluid (CSF) drainage, sedation, temperature management, glucose management, administering an antiepileptic drug or administering a neuroprotective agent. In some embodiments, the CSF drainage comprises the use of a ventricular catheter. In further embodiments, the optimizing venous drainage comprises keeping the head of the subject in neutral position. In yet further embodiments, the osmotic therapy comprises the administration of mannitol or hypertonic saline. In some embodiments, the sedation comprises the administration of a barbiturate, propofol, a benzodiazepine or an opiate. In further embodiments, the antiepileptic drug is phenytoin or valproic acid. In yet further embodiments, the neuroprotective treatment comprises the administration to the subject of progesterone, magnesium, citicoline, cyclosporine or erythropoietin.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

BRIEF DESCRIPTION OF THE DRAWINGS

FIGS. 5A-I illustrate morphological disruptions at the BBB in CCI-TBI as compared to sham surgeries (craniotomy only). The figures show representative images of morphological disruptions of the tight junctions at the BBB; this analysis was performed on the subcortical region outlined by the white squares in FIG. 2 (middle panel). Immunostaining is shown for ZO-1, a critical member of the TJ complex, counterstained with p-glycoprotein (Pgp) which is abundant in the brain endothelium (all magnifications are at 40×). Note that in the sham, there is intense and continuous ZO-1 staining of normal vessels (arrowheads) which provides the characteristic strand-like formation (FIG. 5A). FIGS. 5B and 5C show Pgp and Pgp/ZO-1 staining, respectively, in the same cells. P-gp aids to identify the vessel and shows no apparent gross vessel damage when stained with or without concurrent ZO-1 staining. For moderate CCI-TBI, the disruption can be seen in two ways. First, some of the TJs are identified as having discontinuous to punctuate patterns of ZO-1 immuno-staining (arrows; FIG. 5D). FIGS. 5E and 5F show Pgp and Pgp/ZO-1 staining, respectively, in the same cells. Second, FIG. 5G clearly shows a vessel with TJ staining (arrowhead) and a nearby vessel with little to no staining (arrows). FIGS. 5H and 5I show Pgp and Pgp/ZO-1 staining, respectively, in the same cells. Therefore, compromised TJ integrity is observed by discontinuous and marked decrease in TJ protein immuno-reactivity.

FIG. 9 D illustrates Western blots probed under the same conditions as in FIG. 9C with doxycycline (Dox, 200 ng/ml) for 48 hr. The expression of unfused AcGFP is observed in the cytosolic fraction (lane 2) and not in the membrane fraction (lane 1) both in the presence and in the absence of doxycycline. The levels of membrane-bound AcGFP-CLD5 and AcGFP-OCC shown in the membrane fraction are depleted when in the presence of doxycycline. (M) indicates the membrane fraction; (C) indicates the cytosolic fraction.

FIG. 11 A illustrates a time course for the amount of occludin (OCC)/exosome in serum after moderate CCI-TBI. FIG. 11 B illustrates the detection of TJ protein in exosomes from impacted animals using the Barriosome ELISA. Differences between the various severities of CCI-TBI at 24 hours after injury are shown. The results are shown as the mean±SEM (n=3), * denotes a difference of P<0.001 between the TBI condition and unimpacted control.

DEFINITIONS

Figure 1:
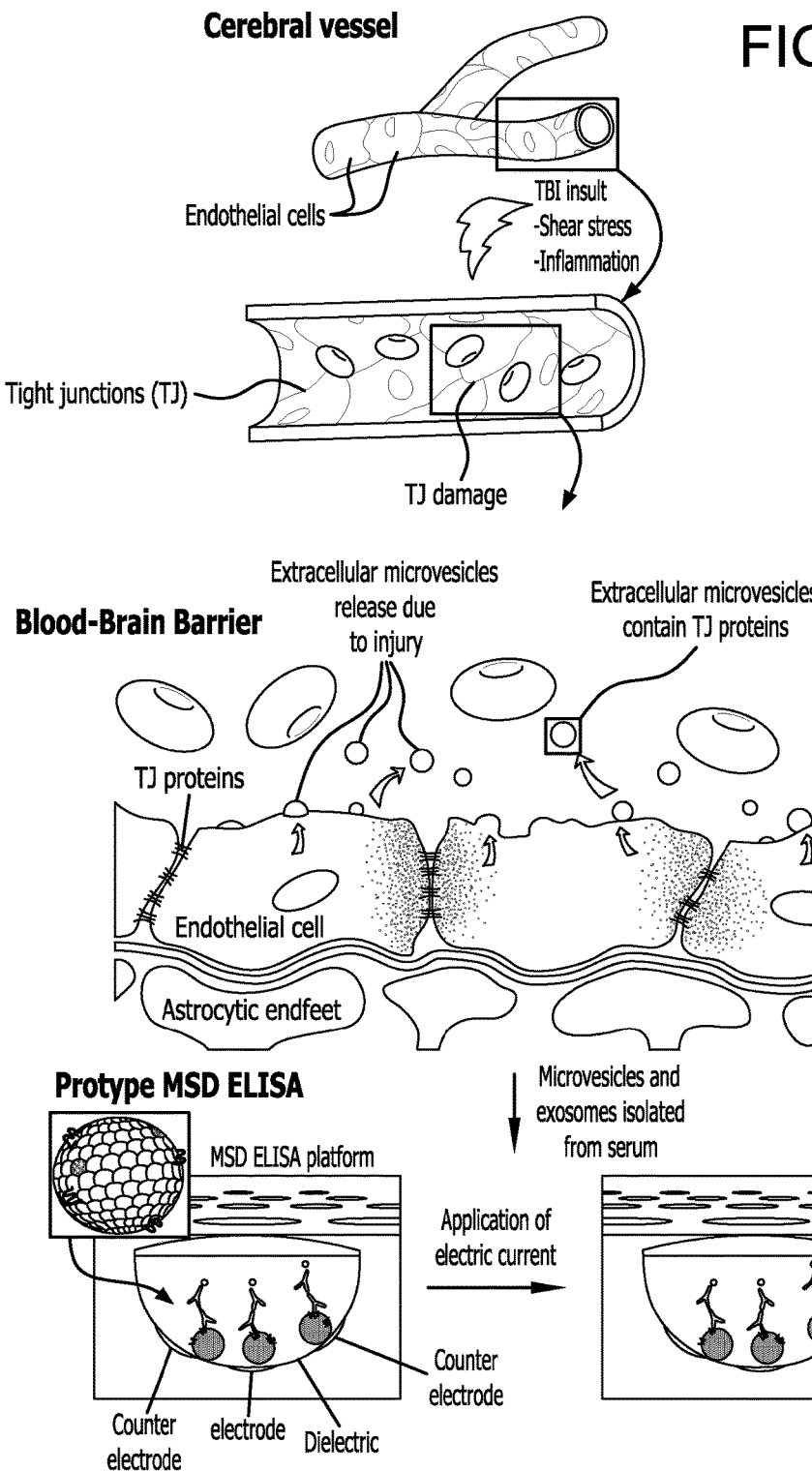
FIG. 1 illustrates a schematic of exosome-based Traumatic Brain Injury (TBI) biomarkers. In this configuration of the prototype Meso Scale Discovery (MSD) ELISA, microvesicles/exosomes coat the bottom of the well and are then probed with specific antibodies to TJ proteins. MSD ELISA is described further in the detailed description below. MSD tag conjugated secondary antibodies are used for detection. Excitation and signal amplification of the MSD tag is generated by electrochemiluminescence. MSD ELISA provides both greater sensitivity and dynamic range than conventional ELISA systems.

As used herein, each of the following terms has the meaning associated with it in this section.

The articles "a" and "an" are used herein to refer to one or to more than one (i.e. to at least one) of the grammatical object of the article. By way of example, "an element" means one element or more than one elements.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "in vitro method," as used herein, refers to a method carried out outside of a living organism as opposed to an "in vivo method" which is a method carried out inside or on a living organism.

The term "injury to the brain," as used herein, refers to any injury to the brain that results in the release of exosomes containing TJ proteins. Injury to the brain comprises traumatic brain injury (TBI), stroke, epilepsy, an inflammatory disease of the brain, an infectious disease to the brain, Chronic Traumatic Encephalopathy (CTE) or Blast Induced Neurotrauma (BINT).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies that may be used in the practice of the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.; Houston et al., 1988, *Proc. Natl. Acad. Sci. USA* 85:5879-5883; Bird et al., 1988, Science 242:423-426).

The term "control" or "reference standard" describes a material comprising a level of a tight junction protein, such that the control or reference standard may serve as a comparator against which a sample can be compared.

The term "blood brain barrier (BBB)," as used herein, describes the boundary that regulates access of blood components (influx of nutrients and efflux of waste) and immune cells into the brain. The BBB separates circulating blood from the brain extracellular fluid (BECF) in the central nervous system (CNS). Brain endothelial cells are connected by tight intercellular junctions, or "tight junctions" (TJ) that provide the physical barrier characteristics of the BBB. TJ formation appears early in brain development greatly restricting the paracellular movement of microscopic objects (such as bacteria), solutes (water-soluble and polar compounds) and small ions into the brain's cerebrospinal fluid (CSF), while allowing the diffusion of small hydrophobic molecules (such as oxygen, carbon dioxide and hormones). Cells of the barrier actively transport metabolic products such as glucose across the barrier with specific proteins.

The term "tight junction (TJ)," as used herein, describes the closely associated area of two cells whose membranes join together forming a virtually impermeable barrier to fluid. Brain endothelial cells are connected by TJs that provide the physical barrier characteristics of the BBB. Brain endothelial tight junction complexes at the molecular level are composed of the following proteins: occludin, claudin (claudin-3, 5, 12), Zonula Occludens protein (ZO-1, 2, 3), and the junction adhesion molecules (JAM-A, B, C) (Abbott N J, Ronnback L, Hansson E. *Nat Rev Neurosci.* 2006. 7(1):41-53). The assembly of the tight junction is such that the intracellular ZO proteins form the major anchoring site for transmembranous occludin, claudin and JAM proteins to bind. In addition, via adaptor proteins the tight junction complex is bridged to the cytoskeleton of the cell. The tight junction complex is central to the interlocking of endothelial cells that give rise to the integrity of the BBB.

The terms "microvesicles," "extracellular vesicles" or "exosomes," as used herein, describe vesicles secreted by endothelial cells of cerebral vessels. Extracellular vesicles also encompass other related terms such as microparticles, ectosomes, apoptotic bodies and multivesicular bodies (exosomes) (Gyorgy, B. et al. *Cell Mol Life Sci* 2011. 68:2667-2688; Cocucci E, Racchetti G and Meldolesi J, Shedding microvesicles: artefacts no more. *Trends Cell Biol* 2009; 19:43-51). These extracellular vesicles are secreted/released membrane vesicles with diverse biological functions. The vesicles are surrounded by a phospholipid bilayer with sizes ranging from 50-100 nm (exosomes) in diameter to 100-1000 nm (microvesicles). In the case of exosomes, the mechanism of release occurs by exocytosis of multivesicular bodies, whereas microvesicles are released by membrane budding or shedding. Because these extracellular microvesicles form from the plasma membrane, cell type specific markers can also be found on the microvesicle identifying the cell type of origin. For example, endothelial cell-specific markers such as CD54, CD62E, CD62P, CD31, CD106, CD105, CD144 and CD146 can be found on the surface of the microvesicle. Additionally, the presence of brain endothelial markers such as Pgp, BCRP, Glut-1, VEGFR-2, transferrin receptor, and Flk-1 could also be present. Identifying exosomal markers such as CD63, CD81, CD9, LAMP1 and TSG101 have been reported to be found in extracellular microvesicles. Although not well understood, the mechanism of microvesicle release has been linked to the induction of cell activation. Microvesicles are typically isolated by differential centrifugation and are detectable by flow cytometry, mass spectrometry, electron or atomic force microscopy or captured based assays.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence which is identical to the mRNA sequence and is usually provided in sequence listings, and the non-coding strand, used as the template for transcription of a gene or cDNA, can be referred to as encoding the protein or other product of that gene or cDNA.

"Gene expression" or "expression" as used herein refers to the process by which information from a gene is made into a functional gene product, such as RNA or protein. Thus, the "level of expression" of a gene product of a marker gene, in a sample of interest, refers to the level of RNA, particularly the level of mRNA, or the level of the encoded protein, and is not intended to be limited to either, unless so specified. "Protein expression," as used herein refers to the level of protein.

The term "ELISA," as used herein, refers to an enzyme-linked immunosorbent assay. The term "ELISA" may refer to either conventional ELISA or to Meso Scale Discovery (MSD) ELISA, both described in the Detailed Description below.

The term "diagnostic procedures," as used herein, comprises procedures to aid in the determination of a disease or to aid in distinguishing one disease from another. Diagnostic procedures related to TBI comprise computed tomography (CT) scanning, magnetic resonance imaging (MRI), X-ray imaging, blood tests, physical examination, cognitive testing, electroencephalography, neuromonitoring, intracranial pressure (ICP) monitoring, assessing cerebral perfusion pressure (CPP) or determining the subject's Glasgow coma scale score (GCS).

The term "treating a disorder or condition associated with an injury to the brain," as used herein, comprises treatment directed to the cure or to the improvement of a disorder or condition associated with an injury to the brain. A disorder or condition associated with an injury to the brain comprises the injury to the brain itself and also disorders or conditions that the patient may suffer from as a result of having sustained an injury to the brain. Treating a disorder or condition associated with TBI comprises, for example, surgical treatment, head elevation, osmotic therapy, hyperventilation, debridement, optimizing venous drainage, cerebrospinal fluid (CSF) drainage, sedation, temperature management, glucose management, administering an antiepileptic drug, administering a neuroprotective agent or administering agents that restore BBB function.

The term "gene" refers to a nucleic acid (e.g., DNA) sequence that comprises coding sequences necessary for the production of a polypeptide, precursor, or RNA (e.g., mRNA, rRNA, tRNA). The term "gene" encompasses both cDNA and genomic forms of a gene.

As used herein, an "instructional material" includes a publication, a recording, a diagram, or any other medium of expression, which can be used to communicate the usefulness of the invention in the kit for determining the progression of a disease. The instructional material of the kit of the invention may, for example, be affixed to a container, which contains a reagent of the invention or be shipped together with a container, which contains a reagent. Alternatively, the instructional material may be shipped separately from the container with the intention that the instructional material and the reagent be used cooperatively by the recipient.

"Measuring" or "measurement," or alternatively "detecting" or "detection," or alternatively "determining" or "determine" means assessing the presence, absence, quantity or amount of either a given substance within a sample, including the derivation of qualitative or quantitative concentration levels of such substances.

"Sample" or "biological sample" as used herein means a biological material that contains a substance under assay for determination of gene product expression level. The sample may contain any biological material suitable for detecting a TJ protein, and may comprise cellular and/or non-cellular material.

The term "solid support," "support," and "substrate" as used herein are used interchangeably and refer to a material or group of materials having a rigid or semi-rigid surface or surfaces. In one embodiment, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

"Specifically binds" as used herein in the context of an antibody or an aptamer refers to antibody or aptamer binding to a predetermined antigen with a preference that enables the antibody to be used to distinguish the antigen from others to an extent that permits the detection of the target antigens described herein.

DETAILED DESCRIPTION OF THE INVENTION

We have found that brain endothelial cells release high levels of exosomes into the bloodstream following brain injury, and that these exosomes contain detectable barrier TJ proteins. Accordingly, detection of BBB TJ proteins may be used for diagnosing injury to the brain, such as TBI, based on analysis of fluids such as blood, blood plasma, blood serum, cerebrospinal fluid or urine.

As described in the examples that follow, TJ protein is a better marker than the standard markers currently used to detect injury to the brain, such as S100β, the currently preferred marker for traumatic brain injury. As illustrated in the examples (see FIG. 12), the level of TJ proteins detected in exosomes is proportional to the extent of injury, whereas S100β is an all-or-nothing marker whose presence indicates that there is injury but whose levels are not proportional to the extent of the injury.

Isolation of Exosomes

To determine the level of TJ protein in exosomes, exosomes can be isolated from blood, blood plasma, blood serum, cerebrospinal fluid, urine or other biological fluids by exosome precipitation. Exosome precipitation methods are well-known in the art. For example, the EXOQUICK™ exosome precipitation reagent (System Biosciences, Mountain View, Calif.) may be employed to precipitate exosomes. The exosomes may then be recovered as a pellet after centrifugation.

Alternatively, the exosomes can be isolated by a series of ultracentrifugations, as illustrated in Example 2. As used herein, "ultracentrifugation" has its conventional meaning in the art. In some embodiments, ultracentrifugation comprises spinning the sample at at least 10,000×g 20,000×g, at least 30,000×g, at least 40,000×g, at least 50,000×g, at least 75,000×g, at least 100,000×g, at least 150,000×g, at least 250,000×g, at least 500,000×g, at least 750,000×g, or at least 100,000×g. Those skilled in the art will appreciate that several of the variables in the Examples can be adjusted while still allowing for enrichment.

The exosomes may further be filtered. Various suitable sizes and types of filtration may be used, including filtering to elute exosome-sized particles in the sample (e.g., >100 nm, 150 nm, 200 nm, 250 nm), filtering to capture exosome-sized particles (e.g., <50 nm, 40 nm, 30 nm, 20 nm, 10 nm), or both combined.

The exosomes may also be isolated by flow cytometry, using an antibody that recognizes an exosome-specific marker such as CD63, or recognizing a TJ protein according to the invention. Such an antibody can be used to select exosomes. Flow cytometry can both sort exosomes (i.e. separate exosomes of interest out of the sample milieu) and quantitate them, as shown in the Examples. One of the advantages of flow cytometry is that multiple markers may be assayed at the same time by analyzing a panel of antigens by cell sorting using antibodies to each antigen and employing a multichannel sorter.

The exosomes may also be isolated by affinity chromatography, using an antibody that recognizes an exosome-specific marker such as CD63, or recognizing a TJ protein according to the invention, attached to a solid support. ELISA may also be used to isolate exosomes, using a primary antibody that recognizes an exosome-specific marker such as CD63, or recognizing a TJ protein according to the invention, attached to a solid support.

An antibody that recognizes an exosome-specific marker such as CD63, or that recognizes a TJ protein according to the invention can therefore be used to select exosomes. Once selected, the exosomes can be used to perform further experiments.

Detection of TJ Proteins

Any methods available in the art for detecting and quantifying a BBB TJ protein from an exosome according to the invention, is encompassed. Such methods may rely on utilizing a substance comprising a binding moiety for the BBB TJ protein. Assays based on BBB TJ protein-specific biomolecule interaction include, but are not limited to, antibody-based assays, aptamer-based assays, receptor and ligand assays, enzyme activity assays, and allosteric regulator binding assays. The invention is not limited to any one method of protein quantification with respect to a control recited herein, but rather encompasses all presently known or heretofore unknown methods, such as methods that are discovered in the art. Proteins may be detected by other methods, e.g., mass spectroscopy analysis, that do not rely on a binding moiety.

In one embodiment, the substance comprises an antibody that specifically binds to a BBB TJ protein. Antibodies can be used in various immunoassay-based protein determination methods such as Western blot analysis, immunoprecipitation, radioimmunoassay (RIA), immunofluorescence assay, chemiluminescence assay, flow cytometry, immunocytochemistry, immunohistochemistry and enzyme-linked immunosorbent assay (ELISA).

In an enzyme-linked immunosorbent assay (ELISA), an enzyme such as, but not limited to, horseradish peroxidase (HRP), alkaline phosphatase (AP), beta-galactosidase or urease can be linked, for example, to an antigen antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Another form of ELISA is Meso Scale Discovery (MSD) ELISA developed by Meso Scale Discovery, Gaithersburg, Md. MSD's electrochemiluminescence detection technology uses SULFO-TAG™ labels, which emit light upon electrochemical stimulation initiated at the electrode surfaces of MULTI-ARRAY® and MULTI-SPOT® microplates. In preferred embodiments, multiwell plates from MSD® are coated with exosomes isolated from cell culture, from serum, from CSF or from blood, for 30 min at room temperature with coating buffer (Meso Scale Discovery, Gaithersburg, Md.). The wells are washed and blocked with MSD® blocking solution, containing 5% BSA in PBS. Primary antibodies diluted in 1×PBS/0.1% Tween 20 are used to detect exosome protein markers such as CD63 and TJ proteins such as occludin, claudin-3, claudin-5, claudin-12, ZO-1, ZO-2, ZO-3, JAM-A, JAM-B or JAM-C. All antibodies are incubated for 1 hour at room temperature under gentle shaking. Bound primary antibodies are exposed to the corresponding species-specific secondary antibody conjugated to the ruthenium(II)-tris-bipyridine ([Ru(bpy)$_3^{2+}$]-containing SULFO-TAG™ (1 u/ml, Meso Scale Discovery, Gaithersburg, Md.) for 1 hour at room temperature under gentle shaking. The plates are rinsed with 1×PBS and 1× read buffer T (MSD®) containing tripropylamine (TPA) is then added, followed by detection using the SECTOR® Imager 2400 MSD. Data analysis is performed using the MSD® DISCOVERY WORKBENCH® Software. Detection is based on electrochemical oxidation of Ruthenium(II)-tris-bipyridine ([Ru(bpy)$_3^{2+}$] in the presence of Tripropylamine (TPA), an electrochemical co-reactant, leading to the efficient generation of electrochemiluminescence glow via the high energy electron transfer reaction between Ru(bpy)$_3^{3+}$ and TPA radical. To normalize the results, the amount of TJ protein detected may be divided by the amount of exosome marker, such as CD63, detected by the assay for each sample. In some embodiments, the primary antibodies are directly bound to SULFO-TAG™.

For chemiluminescence and fluorescence assays, chemiluminescent and fluorescent secondary antibodies may be obtained from any number of commercial sources. Fluorescent detection is also useful for detecting antigen or for determining a level of antigen in a method of the invention. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antigen-specific antibodies.

Radioimmunoassays (RIAs) are described for example in Brophy et al. (1990, Biochem. Biophys. Res. Comm. 167: 898-903) and Guechot et al. (1996, Clin. Chem. 42:558-563). Radioimmunoassays are performed, for example, using Iodine-125-labeled primary or secondary antibody.

Quantitative Western blotting may also be used to determine the level of BBB TJ protein according to the present invention. Western blots are quantified using well known methods such as scanning densitometry (Parra et al., 1998, J. Vasc. Surg. 28:669-675).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis of the amount of antigen is performed using a spectrophotometer. It is understood that the assays of the invention can be performed manually or, if desired, can be automated and that the signal emitted from multiple samples can be detected simultaneously in many systems available commercially.

The antibody used to determine the level of BBB TJ protein in a sample in an immunnoassay can comprise a polyclonal or monoclonal antibody. The antibody can comprise an intact antibody, or antibody fragments capable of specifically binding a BBB TJ protein. Such fragments include, but are not limited to, Fab and F(ab')$_2$ fragments.

When the antibody used in the methods of the invention is a polyclonal antibody (IgG), the antibody is generated by inoculating a suitable animal with a BBB TJ protein, peptide or a fragment thereof. Antibodies produced in the inoculated animal which specifically bind a BBB TJ protein are then isolated from fluid obtained from the animal. Antibodies may be generated in this manner in several non-human mammals such as, but not limited to goat, sheep, horse, rabbit, and donkey. Methods for generating polyclonal antibodies are well known in the art and are described, for example in Harlow, et al. (1988, In: Antibodies, A Laboratory Manual, Cold Spring Harbor, N.Y.). These methods are not repeated herein as they are commonly used in the art of antibody technology.

When the antibody used in the methods of the invention is a monoclonal antibody, the antibody is generated using any well known monoclonal antibody preparation procedures such as those described, for example, in Harlow et al. (supra) and in Tuszynski et al. (1988), Blood, 72:109-115. Given that these methods are well known in the art, they are not replicated herein. Generally, monoclonal antibodies directed against a desired antigen are generated from mice immunized with the antigen using standard procedures as referenced herein. Monoclonal antibodies directed against full length or peptide fragments of a BBB TJ protein may be prepared using the techniques described in Harlow, et al., supra.

Techniques for detecting and quantifying (such as with respect to a control) antibody binding are well-known in the art. Antibody binding to a BBB TJ protein may be detected through the use of chemical reagents that generate a detectable signal that corresponds to the level of antibody binding and, accordingly, to the level of BBB TJ protein present on exosomes. Examples of such detectable substances include enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Antibody binding may be detected through the use of a secondary antibody that is conjugated to a detectable label. Examples of detectable labels include but are not limited to polymer-enzyme conjugates. The enzymes in these complexes are typically used to catalyze the deposition of a chromogen at the antigen-antibody binding site, thereby resulting in cell staining that corresponds to expression level of the protein of interest (in this case a BBB TJ protein). Preferred enzymes of particular interest include horseradish peroxidase (HRP) and alkaline phosphatase (AP).

A protein assay may be employed that combines antibody-protein binding with detection of the reporter nucleic acid by real-time PCR, e.g., TAQMAN® Chemistry-Based Protein Assay, Applied BioSystems by Life Technologies Corporation, Carlsbad, Calif. The latter is a proximity ligation assay based upon Fredriksson el al., *Nat. Biotechnol.* 2002, 20:473-477 and Gullberg et al., *Prot Natl Acad Sci USA*. 2004, 101(22):8420-4.

BBB TJ proteins can be detected and quantified by aptamer-based assays, which are very similar to antibody-based assays, but with the use of an aptamer instead of an antibody. An "aptamer-based" assay is thus an assay for the determination of polypeptide that relies on specific binding of an aptamer. An aptamer can be any polynucleotide, generally a RNA or a DNA, which has a useful biological activity in terms of biochemical activity or molecular recognition attributes. Usually, an aptamer has a molecular activity such as having an enzymatic activity or binding to a polypeptide at a specific region (i.e., similar to an epitope for an antibody) of the polypeptide. It is generally known in the art that an aptamer can be made by in vitro selection methods. In vitro selection methods include a well known method called systematic evolution of ligands by exponential enrichment (a.k.a. SELEX). Briefly, in vitro selection involves screening a pool of random polynucleotides for a particular polynucleotide that binds to a biomolecule, such as a polypeptide, or has a particular activity that is selectable. Generally, the particular polynucleotide represents a very small fraction of the pool, therefore, a round of amplification, usually via polymerase chain reaction, is employed to increase the representation of potentially useful aptamers. Successive rounds of selection and amplification are employed to exponentially increase the abundance of a particular aptamer. In vitro selection is described in Famulok, M.; Szostak, J. W., In Vitro Selection of Specific Ligand Binding Nucleic Acids, *Angew. Chem.* 1992, 104:1001. (*Angew. Chem. Int. Ed. Engl.* 1992, 31:979-988.); Famulok, M.; Szostak, J. W., Selection of Functional RNA and DNA Molecules from Randomized Sequences, *Nucleic Acids and Molecular Biology*, Vol 7, F. Eckstein, D. M. J. Lilley, Eds., Springer Verlag, Berlin, 1993, pp. 271; Klug, S.; Famulok, M., All you wanted to know about SELEX; *Mol. Biol. Reports* 1994, 20:97-107; and Burgstaller, P.; Famulok, M. Synthetic ribozymes and the first deoxyribozyme; *Angew. Chem.* 1995, 107:1303-1306 (*Angew. Chem. Int. Ed. Engl.* 1995, 34:1189-1192), U.S. Pat. Nos. 6,287,765, 6,180,348, 6,001,570, 5,861,588, 5,567,588, 5,475,096, and 5,270,163, which are incorporated herein by reference.

Substantially pure BBB TJ protein, which can be used as an immunogen for raising polyclonal or monoclonal antibodies, or as a substrate for selecting aptamers, can be prepared, for example, by recombinant DNA methods. For example, the cDNA of the BBB TJ protein can be cloned into an expression vector by techniques within the skill in the art. An expression vector comprising sequences encoding the maker protein can then be transfected into an appropriate, for example bacterial, host, whereupon the protein is expressed. The expressed protein can then be isolated by any suitable technique.

For example, a BBB TJ protein can be prepared in the form of a bacterially expressed glutathione S-transferase (GST) fusion protein. Such fusion proteins can be prepared using commercially available expression systems, following standard expression protocols, e.g., "Expression and Purification of Glutathione-S-Transferase Fusion Proteins", Supplement 10, unit 16.7, in *Current Protocols in Molecular Biology* (1990) and Smith and Johnson, *Gene* 1988, 67:34-40; Frangioni and Neel, *Anal. Biochem.* 1993, 210:179-187, the entire disclosures of which are herein incorporated by reference.

Kits

The practice of the invention is readily adapted to kit form. The identification of the link between BBB TJ protein on exosomes and injury to the brain provides the basis for clinical diagnostic kits based on BBB TJ protein detection on exosomes.

Basic materials and reagents required for detection of injury to the brain according to the invention may be assembled in a kit. Provided is a kit for detection of injury to the brain comprising a set of reagents that specifically detects the presence of a BBB TJ protein on exosomes, and instructions for using the kit for detecting injury to the brain. In certain embodiments, the kit comprises at least one reagent that specifically detects the presence of a BBB TJ protein on exosomes, and instructions for using the kit according to one or more methods of the invention. Each kit necessarily comprises reagents which render the procedure specific. For example, for each BBB TJ protein, the kit can comprise an antibody, an antibody derivative, or an antibody fragment that binds specifically with the BBB TJ protein.

Depending on the procedure, the kit may further comprise one or more reagents for the isolation of exosomes from a biological fluid. In preferred embodiments, the biological fluid is blood, blood plasma, blood serum, cerebrospinal fluid or urine. In further preferred embodiments, the blood is peripheral blood. Exosomes can be isolated from blood, blood plasma, blood serum, cerebrospinal fluid, urine or other biological fluids by exosome precipitation. Exosome precipitation methods are well-known in the art. For example, the EXOQUICK™ exosome precipitation reagent (System Biosciences, Mountain View, Calif.) is employed to precipitate exosomes. The exosomes may then be recovered as a pellet after centrifugation. Exosomes can also be isolated by ultracentrifugation, as described above.

Depending on the procedure, the kit may further comprise one or more of: immunodetection buffer and/or reagents, labeling buffer and/or reagents, and detection means. Protocols for using these buffers and reagents for performing different steps of the procedure may also be included in the kit.

Reagents may be supplied in a solid (e.g., lyophilized) or liquid form. Kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps for the disclosed methods may also be provided. In certain embodiments, the kits of the present invention further comprise control samples.

Instructions for using the kit according to one or more methods of the invention may comprise instructions for processing the biological fluid sample and exosome preparation thereof, and/or performing the test, and instructions for interpreting the results.

The kit may also include instructional material that informs the user of the relationship between detection of BBB TJ proteins on exosomes and injury to the brain. The instructional material may comprise a publication, a recording, a diagram, or any other medium of expression which can be used to communicate the usefulness of the method of the invention in the kit for assessment of injury to the brain. The package insert may comprise text housed in any physical medium, e.g., paper, cardboard, film, or may be housed in an electronic medium such as a diskette, chip, memory stick or other electronic storage form. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

For antibody-based kits, the kit can comprise, for example: (1) a first antibody (e.g., attached to a solid support) that binds to a BBB TJ protein on exosomes; and, optionally, (2) a second, different antibody that binds to either the protein or the first antibody and is conjugated to a detectable label. The kit can further comprise components necessary for detecting the detectable label (e.g., an enzyme or a substrate), and instrumentation for detection and measurement. In some embodiments, the BBB TJ proteins are labeled with different colors. A kit may further optionally contain aliquots of known amounts of a BBB TJ protein to serve as reference standards, or reference samples representing BBB TJ protein(s) from a patient with a given type of injury to the brain.

The antibody-based kit for determination of BBB TJ protein on exosomes may further contain a package insert that informs the user of the relationship between level of BBB TJ protein on exosomes and disease prognosis. A decreased level is an indication that the brain injury has lessened.

Applications

In another embodiment, provided is a method for monitoring the progression of brain injury in a subject. Samples are obtained from the subject at different time points and analyzed as described above. An elevated level of BBB TJ protein on exosomes in a later sample relative to an earlier sample is an indication that the brain injury has progressed in the subject.

The methods disclosed herein may also be used to determine the severity of the brain injury (mild to severe brain injury). The extent to which the level of BBB TJ protein on exosomes is elevated in comparison to a control indicates the severity of the injury.

In another embodiment, the methods disclosed herein are used to determine brain injury treatment efficacy. An elevated level of BBB TJ protein on exosomes in a later sample relative to an earlier sample is an indication that the brain injury has progressed in the subject. However, a lower level of BBB TJ protein on exosomes in a later sample relative to an earlier sample is an indication that the brain injury has improved, i.e. that treatment has been effective, in the subject.

The methods disclosed herein may be used to evaluate damage to the BBB, such as damage that occurs in epilepsy. The methods disclosed herein may also be useful in evaluating TBI due to sports related or other types of concussions.

The methods disclosed herein may also be of use to diagnose Chronic Traumatic Encephalopathy (CTE). A newly characterized CTE which develops over long periods of time is a very specific form of neuropathy that shows hyper phosphorylation of tau protei in neurons. CTE is a form of TBI that develops from exposure to repeated sports related concussions.

The methods disclosed herein may also be used to evaluate brain injury due to Blast Induced Neurotrauma (BINT). This may be useful in wartime military engagement where personnel may be exposed to blast waves generated by explosives. Also in the context of military operations, the methods disclosed herein may be developed to be a deployable test that can be used to rapidly assess the brain injury of soldiers exposed to BINT.

The methods disclosed herein may also be used to evaluate injury to the brain related to HIV infection, such as various HIV-1 related encephalopathies (See Example 9). The various HIV-1 related encephalopathies are shown to produce occludin-containing microvesicles/exosomes derived from the BBB, as a result of injury to the brain.

The methods disclosed herein may also be used in an array configuration with other neuronal or glial based TBI biomarkers.

Treatment of Disorders or Conditions Associated with Injury to the Brain.

In embodiments of the invention, detection of brain injury through detection of TJ protein on exosomes of a subject is coupled with appropriate treatment of the brain injury, or treatment of disorders or conditions associated with the brain injury. Those treatments are detailed as follows.

Prevention of Hypotension and Hypoxia

For example, initial treatment of disorders or conditions associated with brain injury includes the prevention of hypotension (systolic blood pressure <90 mmHg) and hypoxia ($PaO_2$<60 mmHg), two systemic insults known to be major causes of secondary injury after TBI (Brain Trauma Foundation, American Association of Neurological Surgeons, Congress of Neurological Surgeons, et al. *J Neurotrauma* 2007; 24 Suppl 1:S7; McHugh G C, Engel D C, Butcher I, et al. *J Neurotrauma* 2007; 24:287; Silverston P. BMJ 1989; 298:711; Stocchetti N, Furlan A, Volta F. *J Trauma* 1996; 40:764; Chestnut R M, Marshall L F, Klauber M R, et al. *J Trauma* 1993; 34:216; Manley G, Knudson M M, Morabito D, et al. *Arch Surg* 2001; 136:1118.) Studies have shown that treatments that attempt to normalize oxygenation and blood pressure have improved outcomes (Andrews P J, Sleeman D H, Statham P F, et al. *J Neurosurg* 2002; 97:326; Clifton G L, Miller E R, Choi S C, Levin H S. *Crit Care Med* 2002; 30:739; Winchell R J, Hoyt D B. *Arch Surg* 1997; 132:592; Rudehill A, Bellander B M, Weitzberg E, et al. *J Neurotrauma* 2002; 19:855; Davis D P, Peay J, Sise M J, et al. *J Trauma* 2010; 69:294). Adequate oxygenation ($PaO_2$>60 mmHg) and blood pressure support (systolic BP>90 mmHg) are therefore priorities after the detection of a brain injury in a subject by employing the methods of the invention.

Neurologic Assessment and Treatment for Impending Herniation

After detection of a brain injury in a subject by employing the methods of the invention, patients should be evaluated by the Glasgow coma scale (GCS). Patients with severe TBI as indicated by Glasgow coma scale (GCS)≤8 (Table 1), and clinical systoms that suggest possible impending herniation from elevated intracranial pressure (unilaterally or bilaterally fixed and dilated pupil(s), decorticate or decerebrate posturing, bradycardia, hypertension, and/or respiratory depression) should be treated urgently, with head elevation, hyperventilation, and osmotic therapy (mannitol 1 g/kg iv) concurrently with neuroimaging and other neurological assessments such as computed tomography (CT) scan and magnetic resonance imaging (MRI). CT is the preferred imaging modality. It will detect skull fractures, intracranial hematomas and cerebral edema. Current guidelines recommend head CT in all TBI patients with a Glasgow coma scale of 14 or lower. (uptodate<dot>com/contents/management-of-acute-severe-traumatic-brain-injury).

TABLE 1

Glasgow coma scale (GCS)

|  | Score |
|---|---|
| Eye opening | |
| Spontaneous | 4 |
| Response to verbal command | 3 |
| Response to pain | 2 |
| No eye opening | 1 |
| Best verbal response | |
| Oriented | 5 |
| Confused | 4 |
| Inappropriate words | 3 |
| Incomprehensible sounds | 2 |
| No verbal response | 1 |
| Best motor response | |
| Obeys commands | 6 |
| Localizing response to pain | 5 |
| Withdrawal response to pain | 4 |
| Flexion to pain | 3 |
| Extension to pain | 2 |
| No motor response | 1 |

The GCS is scored between 3 and 15, 3 being the worst, and 15 the best. It is composed of three parameters: best eye response (E), best verbal response (V), and best motor response (M). The components of the GCS should be recorded individually; for example E2V3M4 results in a GCS score of 9. A score of 13 or higher correlates with mild brain injury; a score of 9 to 12 correlates with moderate injury; and a score of 8 or less represents severe brain injury.

Surgical Treatment

After detection of a severe brain injury in a subject by employing the methods of the invention, indications for emergency surgery are based upon neurologic status, usually defined by the GCS (Table 1), and the results of a CT scan, indicating a large hematoma volume or thickness and evidence of mass effect including midline shift. Treatment of epidural hematoma, subdural hematoma and intracerebral hemorrhage includes surgical treatment to evacuate the hematoma or hemorrhage. (Bullock M R, Chestnut R, Ghajar J, et al. *Neurosurgery* 2006; 58:S7; Bullock M R, Chestnut R, Ghajar J, et al. *Neurosurgery* 2006; 58:S16; Bullock M R, Chestnut R, Ghajar J, et al. *Neurosurgery* 2006; 58:S47; Bullock M R, Chestnut R, Ghajar J, et al. *Neurosurgery* 2006; 58:S25). Debridement and dural closure is recommended for penetrating injury. This is to prevent CSF leak. (Surgical management of penetrating brain injury. *J Trauma* 2001; 51:S16; Antibiotic prophylaxis for penetrating brain injury. *J Trauma* 2001; 51:S34).

Elevation and debridement are recommended for open skull fractures depressed greater than the thickness of the cranium or if there is dural penetration, significant intracranial hematoma, frontal sinus involvement, cosmetic deformity, wound infection or contamination, or pneumocephalus (Bullock M R, Chestnut R, Ghajar J et al. *Neurosurgery* 2006. 58:S56). Another treatment for TBI is a decompressive craniectomy, where a substantial portion of the skull is removed in order to reduce intracranial pressure (ICP). (Compagnone C, Murray G D, Teasdale G M, et al. *Neurosurgery* 2005. 57:1183).

Intracranial Pressure (ICP) Monitoring

After detection of a brain injury in a subject by employing the methods of the invention, elevated ICP in the subject should be treated to target pressures below 20 mmHg.

Simple treatments to reduce intracranial pressure include elevating the head of the bed to 30 degrees, optimizing venous drainage by keeping the neck in neutral position, and monitoring central nervous pressure and avoiding excessive hypervolemia. Indications for ICP monitoring include a GCS score <8 and an abnormal CT scan showing evidence of mass effect from lesions such as hematomas, contusions, or swelling. (Brain Trauma Foundation, American Association of Neurological Surgeons, Congress of Neurological Surgeons, et al. *J Neurotrauma* 2007; 24 Suppl 1:S37). ICP monitoring in severe TBI patients with normal CT scan may be indicated if two of the following features are present: age >40 years, motor posturing, systolic BP <90 mmHg. A ventricular catheter connected to a strain gauge transducer is the most accurate and cost-effective method of ICP monitoring and has the therapeutic advantage of allowing for CSF drainage to treat rises in ICP.

Osmotic Therapy

After detection of a brain injury in a subject by employing the methods of the invention, another treatment for brain injury that may be employed involves decreasing the ICP by osmotic therapy. In osmotic therapy, the intravascular injection of hyperosmolar agents creates an osmolar gradient, drawing water across the blood-brain barrier. This leads to a decrease in interstitial volume and a decrease in ICP. Mannitol is the agent used most consistently to achieve ICP control, and it also increases cerebral blood flow. (Brain Trauma Foundation, American Association of Neurological Surgeons, Congress of Neurological Surgeons, et al. *J Neurotrauma* 2007; 24 Suppl 1:S14.) Hypertonic saline may also be used with varying volumes and tonicity (3 to 23.4%) and as either a bolus or as a continuous infusion (Shackford S R, Bourguignon P R, Wald S L, et al. *J Trauma* 1998; 44:50; Ware M L, Nemani V M, Meeker M, et al. *Neurosurgery* 2005; 57:727).

Hyperventilation

After detection of a brain injury in a subject by employing the methods of the invention, another treatment for brain injury that may be employed involves hyperventilation to reduce ICP. With hyperventilation, $PaCO_2$ decreases thereby leading to cerebral vasoconstriction, which then results in decreased cerebral blood volume and ICP. However, $PaCO_2$ of less than 30 mmHg should be avoided, to avoid secondary ischemia brought about by hyperventilation-induced vasoconstriction. (Diringer M N, Yundt K, Videen T O, et al. *J Neurosurg* 2000. 92:7).

Sedation

Another treatment for brain injury that may be employed after detection of a brain injury in a subject by employing the methods of the invention involves sedation and pharmacological paralysis. Sedation and pharmacological paralysis is often used to treat TBI and elevated ICP. Sedation may lower ICP by reducing metabolic demand. Barbiturate coma, for example, pentobarbital has been traditionally used. Propofol may also be used. However, to avoid propofol infusion syndrome, when used in TBI it is suggested that the infusion rate of propofol not exceed 4 mg/kg per hour and that patients be monitored for ECG changes, lactic acidosis, and elevations in creatine kinase and myoglobin. (Ottespoor L C, Kalkman C J, Cremer O L. *Curr Opin Anaesthesiol* 2008; 21:544; Sabsovich I, Rehman Z, Yunen J, Coritsidis G. *Am J Crit Care* 2007; 16:82).

Other sedatives that may be used comprise benzodiazepines, opiates (e.g. midazolam, morphine, fentanyl) individually or in combination with barbiturates and/or neuromuscular blockade. (Brain Trauma Foundation, American Association of Neurological Surgeons, Congress of Neurological Surgeons, et al. *J Neurotrauma* 2007; 24 Suppl 1:S71; Olivecrona M, Zetterlund B, Rodling-Wahlstrom M, et al. *J Neurosurg* 2009; 110:300; Adelson P D, Bratton S L, Carney N A, et al. *Pediatr Crit Care Med* 2003; 4:S34).

Assessment of Cerebral Perfusion Pressure

Cerebral perfusion pressure (CPP) is the difference between mean arterial pressure and ICP. It should be continuously assessed in subjects in which a brain injury has been detected by the methods of the invention. The suggested CCP target is 60 mmHg, avoiding CPP >70 mmHg and <50 mmHg. This should be achieved by optimizing ICP first and then mean arterial pressure, with volume expansion and pressors, second.

Antiepileptic Drugs

The use of antiepileptic drugs (AEDs) in the acute management of TBI has been shown to reduce the incidence of early seizures, but does not prevent the later development of epilepsy, according to some studies. (Temkin N R, Dikmen S S, Wilensky A J, et al. *N Engl J Med* 1990; 323:497; Schierhout G, Roberts I. *Cochrane Database Syst Rev* 2001; CD000173). After detection of a brain injury in a subject by employing the methods of the invention, prophylactic treatment may be carried out with antiepileptic drugs. Antiepileptic drugs that are recommended for prophylactic treatment after TBI include phenytoin and valproic acid.

Temperature Management

After detection of a brain injury in a subject by employing the methods of the invention, temperature management is crucial. Treatment for fever after TBI includes the use of antipyretic medications, surface cooling devices, and endovascular temperature management catheters. Induced hypothermia may also be used to treat TBI.

Glucose Management

After detection of a brain injury in a subject by employing the methods of the invention, glucose management is also crucial. Treatment for TBI includes the management of hyperglycemia and hypoglycemia. Insulin is the preferred treatment for hyperglycemia.

Thromboprophylaxis

After detection of a brain injury in a subject by employing the methods of the invention, treatment with antithrombotic agents is recommended for the prevention of venous thromboembolism. The use and timing of antithrombotic agents is individualized based upon an assessment of the competing risks of venous thrombosis and intracranial hemorrhage expansion. Patients that are not receiving antithrombotic agents should wear pneumatic compression stockings.

Neuroprotective Treatment

After detection of a brain injury in a subject by employing the methods of the invention, neuroprotective treatment may be administered to the subject. The use of a wide range of agents targeting various aspects of the brain injury cascade has been tested in clinical trials. Agents for neuroprotective treatment include progesterone, magnesium, citicoline, cyclosporine and erythropoietin, among others. (Wright D W, Kellerman A L, Hertzberg V S, et al. *Ann Emerg Med* 2007. 49:391; Arango M F, Bainbridge D. *Cochrane Database Syst Rev* 2008. CD005400; Zafonte R, Friedewald W T, Lee S M, et al. *J Neurotrauma* 2009. 26:2207; Mazzeo A T, Brophy G M, Gilman C B, et al. *J Neurotrauma* 2009. 26:2195; Xiong Y, Mahmood A, Chopp M. *Expert Opin Emerg Drugs* 2009. 14:67; Talving P, Lustenberger T, Kobayashi L, et al. *Ann Surg* 2010. 251:1; Velmahoos G C. *Ann Surg* 2010. 251:5).

Advanced Neuromonitoring

After detection of a brain injury in a subject by employing the methods of the invention, the condition of the subject may be followed by advanced neuromonitoring techniques. These techniques supplement ICP monitoring and allow for the measurement of cerebral physiologic and metabolic parameters related to oxygen delivery, cerebral blood flow and metabolism with the goal of improving the detection and management of secondary brain injury. Current monitoring techniques include: jugular venous oximetry, brain tissue oxygen tension monitoring, cerebral micodialysis and thermal diffusion flowmetry. (Cruz J. *Crit Care Med* 1998. 26:344; Brain trauma Foundation, American Association of Neurological Surgeons, congress of Neurological Surgeons, et al. *J Neurotrauma* 2007. 24 Suppl 1:S65; Maloney-Wilensky E, Gracias V, Itkin A, et al. *Crit Care Med* 2009. 37:2057; Stiefel M F, Spiotta A, Gracias V H, et al. *J Neurosurg* 2005. 103:805; Goodman J C, Robertson C S, *Curr Opin Grit Care* 2009. 15:110).

The practice of the invention is illustrated by the following non-limiting examples. The invention should not be construed to be limited solely to the compositions and methods described herein, but should be construed to include other compositions and methods as well. One of skill in the art will know that other compositions and methods are available to perform the procedures described herein.

EXAMPLES

Example 1. Characterization of the Spectrum of Altered TJ Protein Expression in CNS Vessels after TBI The following experiments were carried out to evaluate the status of TJ integrity in the brain following injury using the Controlled Cortical Impact (CCI) model.

Traumatic Brain Injury (TBI) by Controlled Cortical Impact (CCI)

Using the Controlled Cortical Impact (CCI) experimental mouse model of TBI the status of the T J integrity following injury was evaluated (Elliott M B, Jallo J J, Barbe M F, Tuma R F. *Brain Res.* 2009. 1305:183-91). The animal protocol used for these studies has undergone full review and approval (#3415, approved on Nov. 9, 2010) by the Temple University School of Medicine Institutional Animal Care and Use Committee (IACUC). A week after arrival, CS7BL/6 mice (purchased from Taconic Inc, Hudson, N.Y.) were placed into the following groups: untreated (no craniotomy and no TBI), craniotomy only (sham control), mild CCI-TBI, moderate CCI-TBI and severe CCI-TBI. Anesthesia was administered by i.p. injection of ketamine at 100 mg/kg and xylazine at 10 mg/kg. A second bolus of ketamine (50 mg/kg) and xylazine (5 mg/kg) was administered I.P. at 20-30 minutes into the surgery. Depth of anesthesia was monitored every 10 minutes and assessed by both toe and pinna pinch tests. Once the mouse was fully anesthetized, the head was positioned in a stereotaxic frame (Stoelting Instruments, Wood Dale, Ill.) with the nose bar set at zero. The craniotomy was performed lateral to the sagittal suture, and centered between lambda and bregma. A 1-cm square area of skin on the dorsal surface of the skull over the right cortical hemisphere was excised and the periosteum removed. The craniotomy was performed by generating a 4-mm diameter circular osteotomy with a high-speed drill (Champ-Air Dental Drill Benco Dental, Dallas, Tex.) over the right parietal cortex extending from attachment of the temporal muscle to the midpoint of the sagittal suture in the coronal direction and aligned to the middle of the sagittal suture. A cortical contusion was then produced on the exposed brain cortex using a stainless steel impactor tip (3.0 mm in diameter) attached to a magnetically activated piston (Impact One from My Neurolab Inc, Richmond, Ill.). The tip was placed at an angle of 10° to insure that the surface of the impact tip and cortex are parallel at the time of impact. For the different grades of injury raging from mild to severe TBI, the impact tip was set to travel at a velocity of either 1.5 m/s, 3.5 m/s or 5.0 m/s respectively. The impact was also set to compress the cortex by a depth of 1.0 mm during 0.1 sec of contact. Following injury, the bone flap was replaced and sealed with bone wax then the skin sutured closed. For imaging studies, a 5-mm coverslip was introduced over the exposed brain and an airtight seal was generated using Nexaband Quick Gel. The tissue adhesive quickly created a waterproof seal between the edge of the skin and the glass coverslip. Of importance, the tissue adhesives which are also FDA approved are stable over weeks and show no histotoxicity. During the procedure and thereafter, the animal was placed on a thermal blanket to prevent any immediate post-traumatic hypothermia until consciousness is regained (determined by righting reflex and increased mobility). Animals in each experimental group were also further subdivided into groups representing time points 0 hrs, 5 hrs, 24 hrs, 48 hrs, 72 hrs and 7 days post-TBI. For the "sham" designated animals, the mice received the craniotomy but no cortical contusion.

Figure 2:
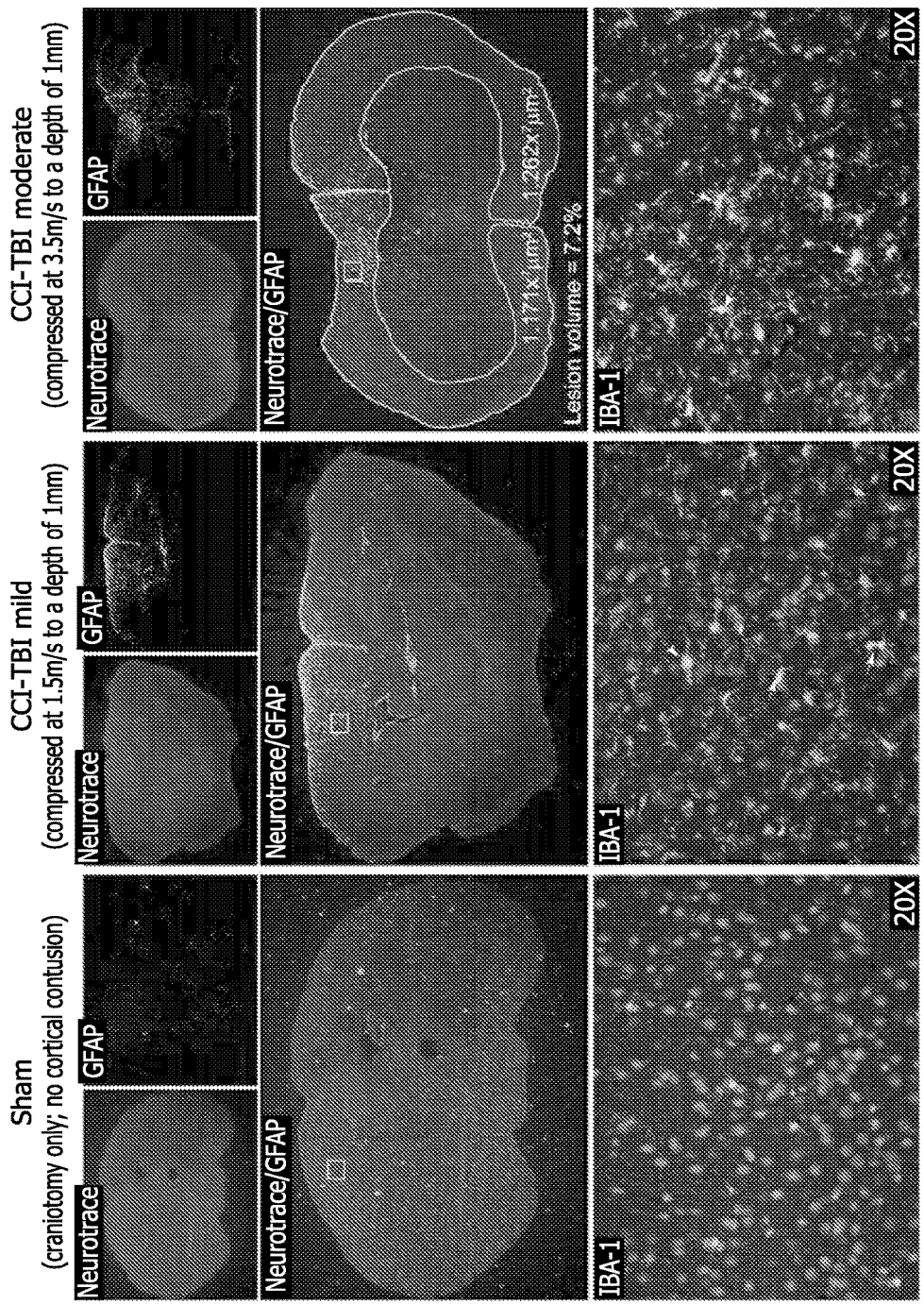
FIG. 2 illustrates brain sections from a sham, mild and moderate controlled cortical impact-traumatic brain injury (CCI-TBI) impacted animals (7 days post injury). The samples were collected at day 7 post-injury and the parameters used for the contusion are shown in the figure. Inflammation such as gliosis is manifested by the increase in glial fibrillary acidic protein (GFAP) immuno-reactivity and the presence of reactive microglia (IBA-1; lower panels). In the case of moderate CCI-TBI, note also the development of cavitation resulting in 7.2% tissue loss.
Figure 3:
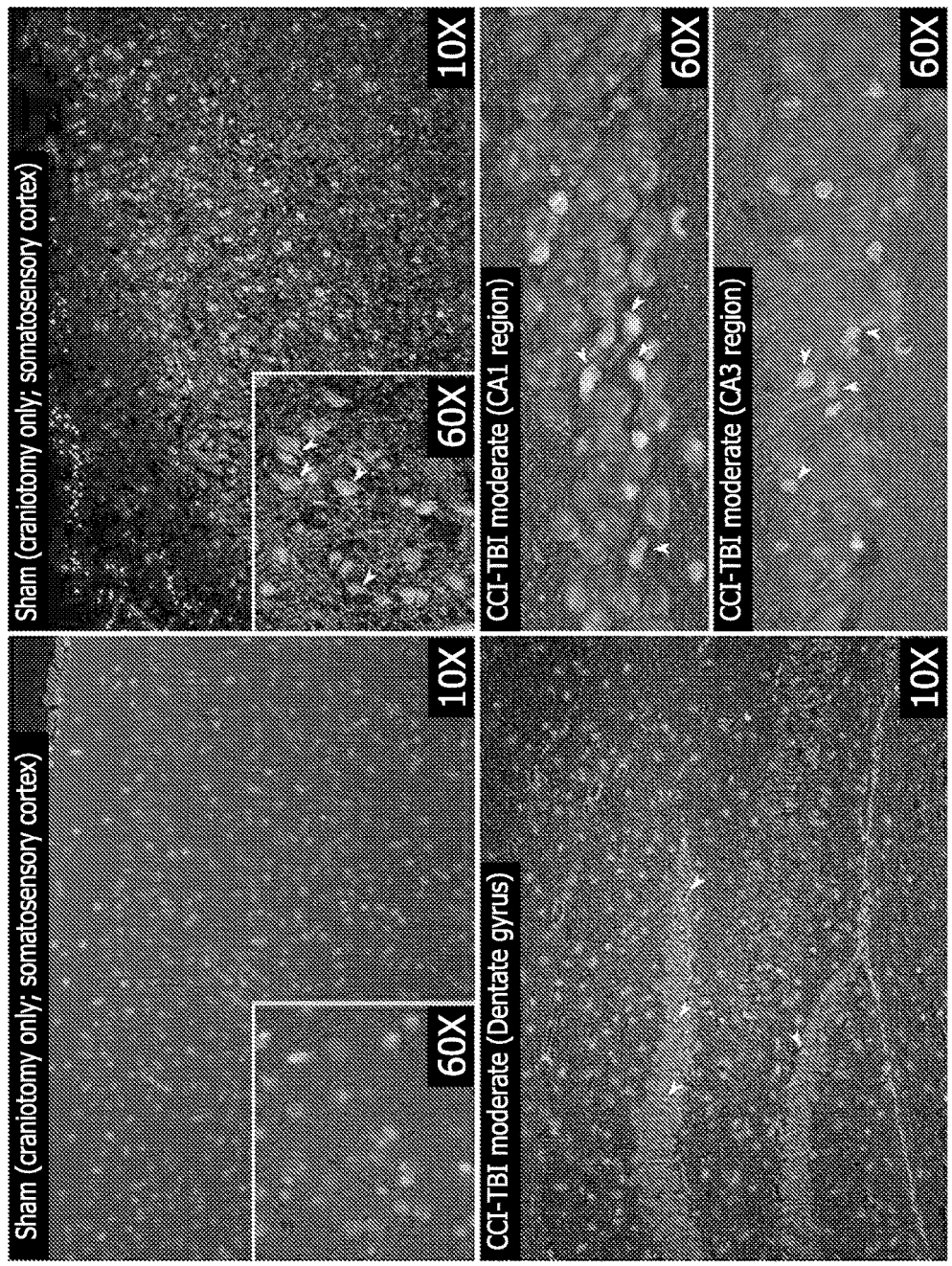
FIG. 3 illustrates neurodegeneration in the cortex and hippocampus ipsilateral of the CCI-TBI. Brain tissue sections from moderate CCI-TBI (7 days post injury) were prepared with JB4 plastic resin, sectioned at 5 microns and stained with fluoro jade B. Cells with high intensity staining for fluoro jade B signify that neurons are undergoing degeneration and cell death. Focal to the site of injury (somatosensory region) great numbers of dying neurons are stained with fluoro jade B. Neurodegeneration is also observed in the dentate gyrus and cornu ammonis (CA) regions of the hippocampal formation which suggests that CCI-TBI can also induce brain injury distal to the impact site (i.e. diffuse injury).
Figure 4:
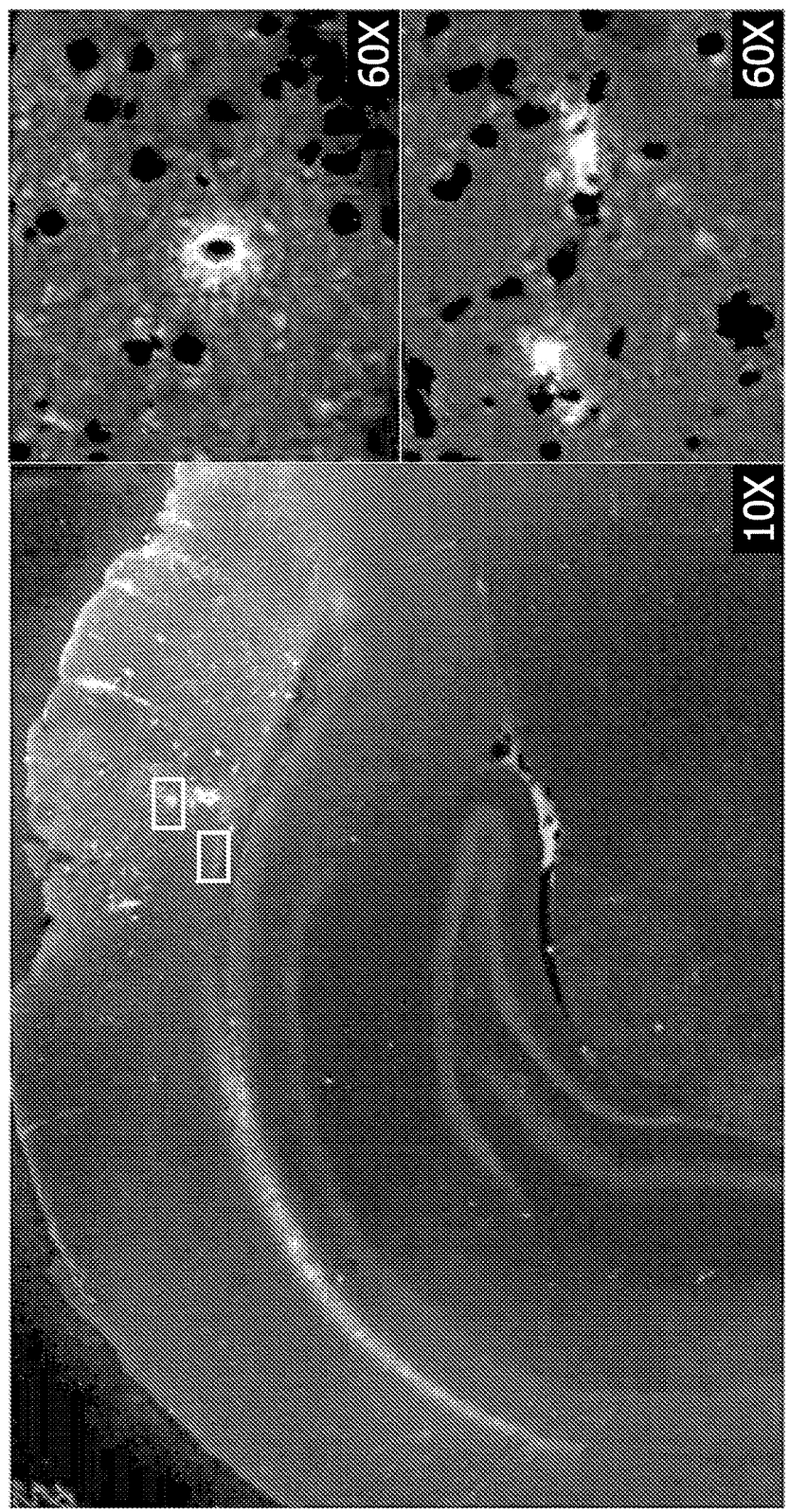
FIG. 4 illustrates BBB permeability post CCI-TBI. The images represent immunolabeling for fibrinogen in brain tissue sections from CCI-TBI (24 hrs). Fibrinogen is normally exclusively found in the vascular compartment and not in the brain parenchyma. After TBI, leakage of blood products occurs and therefore fibrinogen can be detected in the perivascular space and brain parenchyma. Images magnified 60× clearly show extravasation of fibrinogen around microvessels.

The CCI-TBI model consistently reproduced the expected and clinically relevant inflammatory response and neurodegeneration of TBI (FIGS. 2 and 3) (Longhi L, Gesuate R, Perego C, Ortolano F, Sacchi N, Villa P. et al. *J. Cereb Flow Metab.* 2011 September; 31(9):1919-1929; Elliott M B, Tuma R F, Amenta P S, Barbe M F, Jallo J I. *J Neurotrauma.* 2011; 28(6):973-81). Typical findings at 7 day post-TBI (moderate impact 3.5 m/s) include the presence of gliosis observed by high and concentrated GF AP immunoreactivity. Microglia, identified by IBA-1 positive staining, shows a shift from their ramified resting configuration to the activated amoeboid-like morphology in and around the lesion area. Extensive neurodegeneration was also evident, and clearly observed using an in-lab developed method that combines Fluoro-Jade B staining and JB4 plastic resin embedded tissue (FIG. 3). Apart from the neurodegeneration observed focal to the injury site, diffused neurodegeneration was also observed in distal areas such as the dentate gyrus (shown in FIG. 3). The model also induced significant BBB breach. As can be seen in FIG. 4, immunofluorescence labeling of fibrinogen revealed numerous vessels where fibrinogen was accumulated in the perivascular space and through-out the brain parenchyma. The sham group in which only the craniotomy was performed had no detectable TBI related pathology.

BMVEC Isolation and Cell Culture

BMVEC were isolated as previously described (Bernas M J, Cardoso F L, Daley S K, Weinand M E, Campos A R, Ferreira A J, et al. *Nat Protoc.* 2010; 5(7): 1265-72). The hCMEC/D3 cell line provided by Dr. Pierre Couraud from the Cochin Institute (Paris, France), exhibits similar properties as those seen in primary BMVEC and are routinely used in in vitro modeling of the BBB as described (Weksler B B, Subileau E A, Perriere N, Charneau P, Holloway K, Leveque M, et al. *FASEB J.* 2005; 19(13):1872-4). A third cell line, Murine brain-derived capillary endothelial cell line, b-End3, was purchased from the ATCC.

Histology

Following TBI or sham treatment, animals were euthanized and the brain tissue was harvested. The brain was divided into 2-mm coronal sections using a mouse brain matrix (Kent Scientific, Torrington, Conn.) followed by embedding in O.C.T reagent (ThermoFisher scientific Waltham, Mass.) and freezing with 2-methylbutane on liquid nitrogen. For assessment of neurodegeneration, mice were transcardially perfused with 4% formaldehyde, followed by embedding of the brain in glycol methacrylate resin (JB4, Polysciences Inc, Warrington, Pa.). Neurodegeneration was assessed by cutting JB4 embedded sections at 3 microns and then staining with Fluoro-Jade B (Chemicon Millipore, Billerica, Mass.). Indirect immunofluorescence of BBB permeability, TJ proteins, endothelial markers and reactive microglia was performed on serial sections cut at 15-20 microns thick. Serial sections were fixed with methanol and acetone (1:1 v/v) for 20 min at 20° C. and then blocked in 5% normal goat serum for 1 hr. For evaluation of TJ abnormality, antibodies to the following targets and dilutions were used: ZO-1 (1:100, Invitrogen, Carlsbad, Calif.), ZO-2 (1:100, Invitrogen), occludin (1:50, Invitrogen), Claudin-1 (1:50, Abcam, Cambridge, Mass.), Claudin-3 (1:50, Abcam) and Claudin-5 (1:50, Abcam). Evaluation for BBB permeability was performed by immunostaining with fibrinogen antibodies (1:100, Dako, Carpinteria, Calif.). Immunolabeling of endothelial markers was performed with antibodies to p-glycoprotein (Pgp, 1:100, Abcam) or the glucose transporter-1 (Glut-I, 1;50, Abcam) or CD311PCAM-1 (1:50, Abcam). Microglial detection was performed with antibodies to CD163 (1:200, Santa Cruz Biotech, Santa Cruz, Calif.) or IBA-1 (Wako, Osaka, Japan). The following phospho-specific antibodies were used for immunofluorescence: antibodies detecting occludin phosphorylation at threonine 382 or serine 507 or serine 490 and claudin-5 phosphorylation at threonine 207. Comparative semi-quantitative image analysis of the immunofluorescence was performed from images obtained from up to 5 fields per area of interest (i.e cortical, subcortical, dentate gyrus, thalamus etc). Image analysis was performed using Axiovision imaging analysis software (Carl Zeiss microimaging, Germany) using equal acquisition parameters (i.e exposure times) under 40× and 60× objective magnification. Since vessel caliber is an important parameter for evaluating TJ abnormality, the analysis took into account measurements performed in vessel less than 20 microns versus those of 20 microns and above. A line profile for integrated intensity (average optical densities from all the pixels measured) was used to evaluate TJ protein immunofluorescence. The tight junction intensity profiles were categorized as follows: high intensity and continuous (no abnormality), multiple peaks of intensity showing discontinuity (TJ abnormality 1), or an intensity of more than 80% of normal (TJ abnormality 2). Reactive microglia, positive for microglial marker and displaying an amoeboid morphology were measured by particle-counting (using segmentation analysis) and shown as number of cells per area. Neurodegeneration was also analyzed by particle-counting of Fluoro-jade B positive cells and shown as number of cells per area (Axiovision software, Carl Zeiss).

Immunostaining of Endothelial TJs

The integrity of the BBB was studied by immunostaining of the endothelial tight junctions (TJ). The CCI-TBI model was used to investigate the effects of brain injury on endothelial TJ. TJ dysfunction was assessed by histological analysis using antibodies to the various tight junction proteins on brain tissue harvested from mice exposed to increased TBI severity. Animals were placed in one of the following groups: no craniotomy, craniotomy only, mild TBI, moderate TBI and severe TBI. To investigate the progression of changes to the TJs, the above groups were further subdivided into 5 hrs, 24 hrs, 48 hrs, 72 hrs and 7 days post injury. At the indicated time point, brain tissue was harvested, embedded and cryosectioned at 15-20 microns. Using immunolabeling and confocal microscopy the incidence of TJ abnormality in cortical and subcortical areas was evaluated by stereology.

Figures 5D, 5E, 5F:
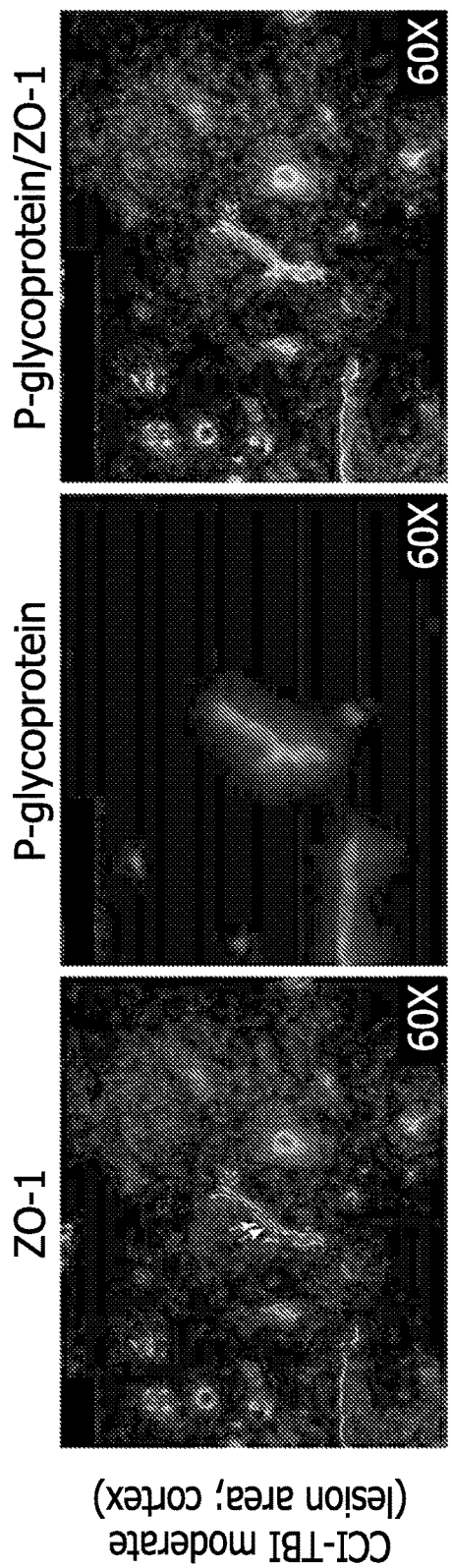
Figures 5G, 5H, 5I:
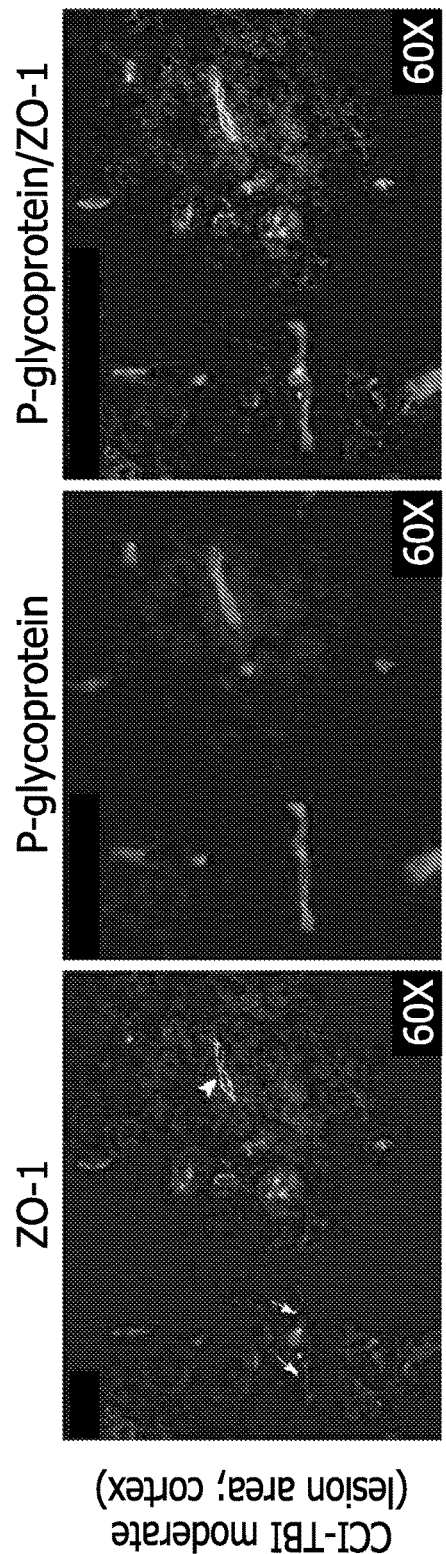

The status of ZO-1 (FIG. 5), an essential submembranous anchor TJ protein, was evaluated (Abbott N J, Ronnback L, Hansson E. Astrocyte-endothelial interactions at the blood-brain barrier. *Nat Rev Neurosci.* 2006; 7(1):41-53). Vessel diameters raging from 5-30 microns were assessed on sections that also included counterstaining for vessel marker, p-glycoprotein (Pgp). The vessel counterstain served to provide a visual guide for tracking the irregular course of the vessel and the second was to allow identification of gross vessel morphology. Compared with the sham control, assessment of the TJ integrity revealed significant disruptions to the TJ s in the TBI group (FIG. 5). Vessel TJ that were considered normal in appearance displayed an intense and continuous pattern of staining as seen in the sham control (FIG. 5, top left panel). In contrast, a significant number of TJs on the ipsilateral and contralateral side of the injury were identified as having discontinuous/punctate patterns of staining (FIG. 5, middle left panel). Interestingly, in some areas, many microvessels clearly identified by P-glycoprotein, were found to have little to no ZO-1 staining (FIG. 5, bottom left panel). Therefore, even though the endothelial lining appeared intact by the Pgp staining, the function of the BBB could be compromised due to a lack of tight junction presence. Changes to the TJ also progress over time.

Figure 6:
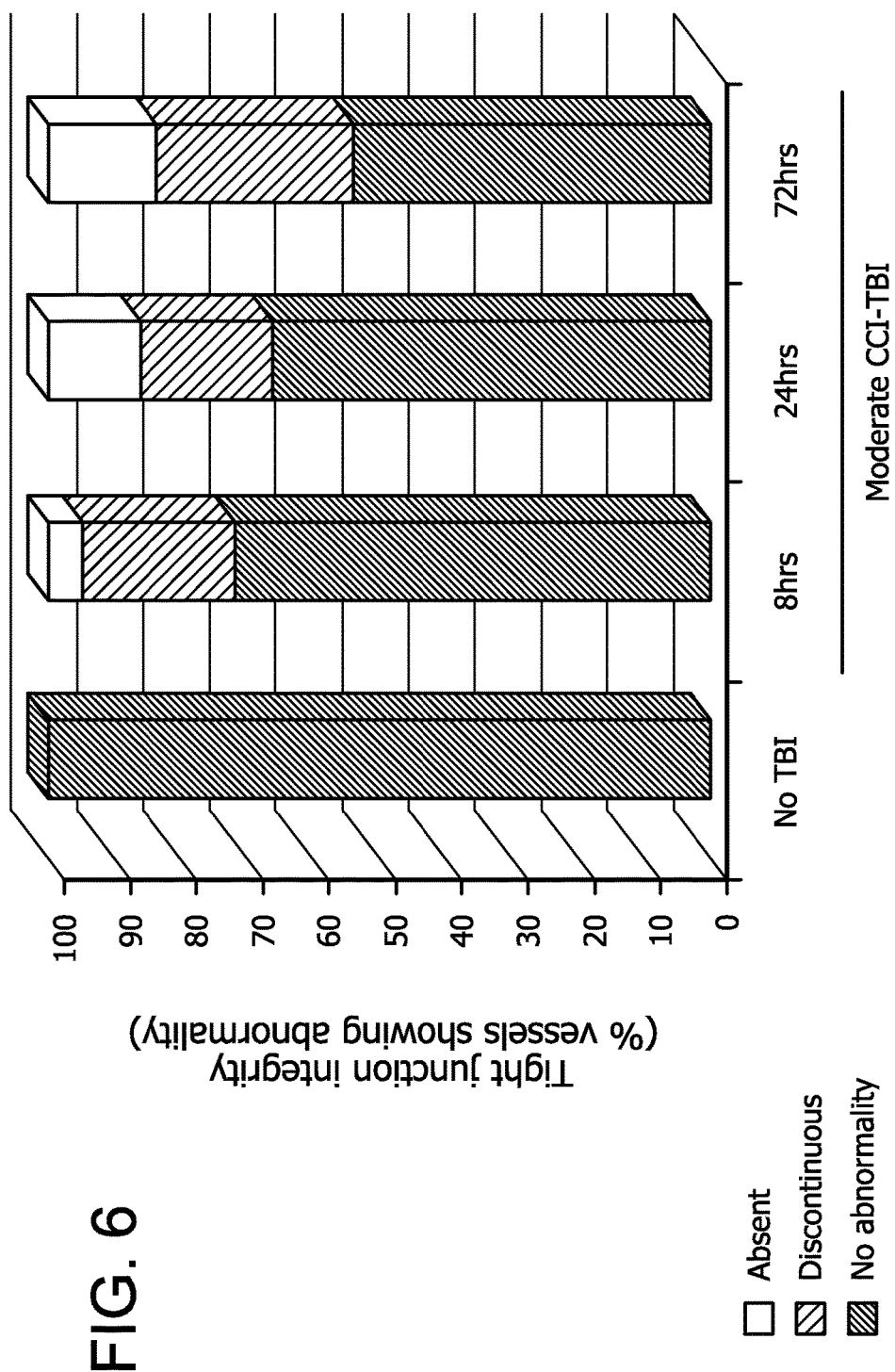
FIG. 6 illustrates occludin abnormality in the cortex of CCI-TBI. A comparative image analysis of TJ abnormality is shown by immunolabeling for occludin in the somatosensory cortex of moderately impacted animals. Vessels ranging in diameter from 10-30 microns were evaluated to determine if TJ staining was of normal appearance (continuous), or if TJ staining was altered (puctate/discontinuous or absent). A total of 150 vessels (for each time point) of 50 microns in length were observed in multiple fields under 40× objective power.

A quantitative analysis of TJ protein occludin in the sematosensory cortex showed similar patterns of TJ disruption as a function of time in moderate TBI as were observed for ZO-1 (FIG. 6).

Statistical Analysis

Where indicated, the data is expressed as the average±SEM. Statistical evaluations for multiple group comparisons were performed by one-way ANOVA (analysis of variance) with Dunnett's post-hoc tests. In certain cases paired two-tailed Student's t-test was used to compare before and after effects. Data lacking normal distribution was analyzed with the appropriate non-parametric method (Kruskal-Wallis test). Statistical analyses was performed utilizing Prism v5 software (GraphPad Software Inc., La Jolla, Calif.) or MedCalc software (Belgium) for ROC determinations.

Figure 7A:
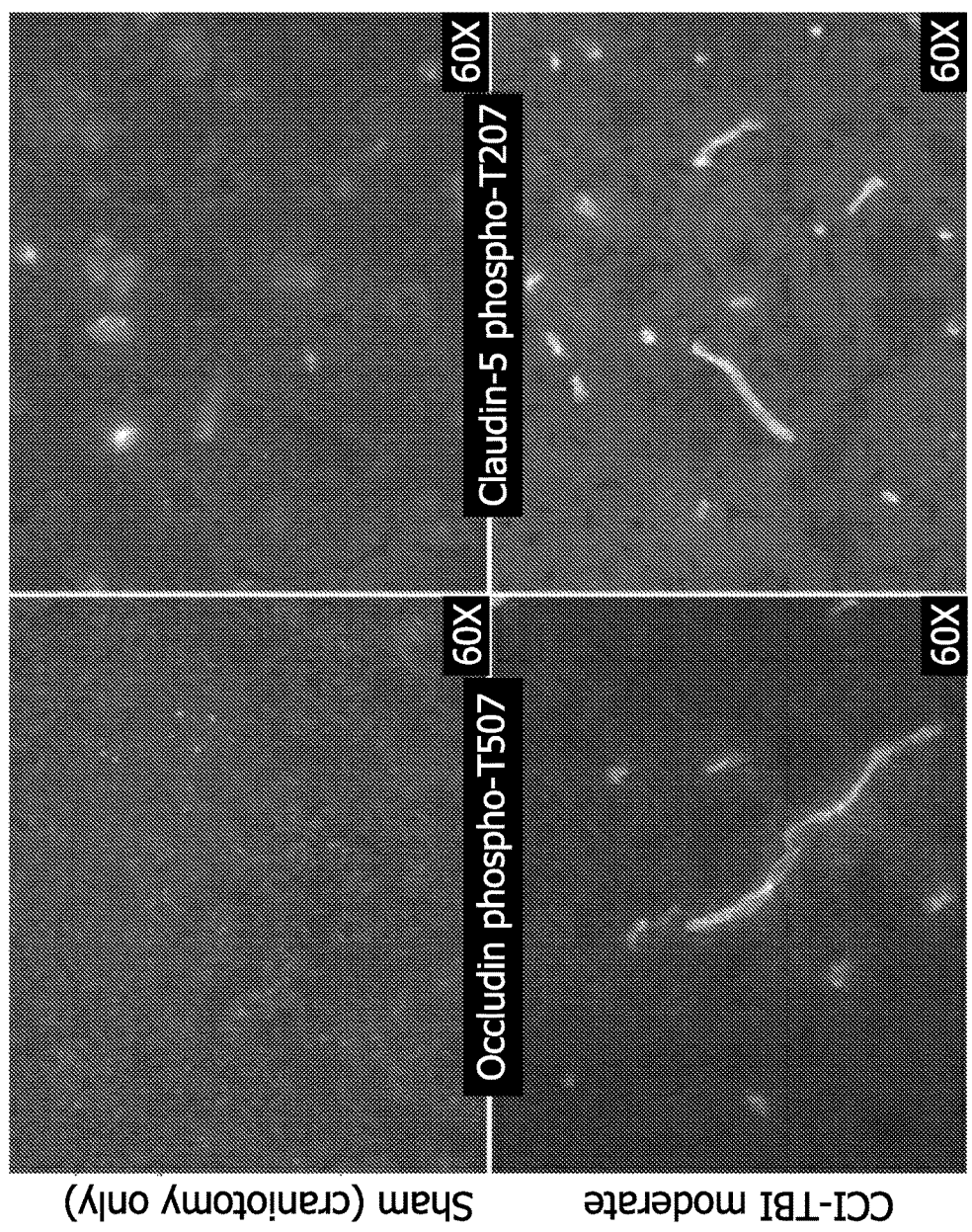
FIG. 7A illustrates staining of brain sections (striatum) of impacted animals with phosphor-specific antibodies to occludin and claudin-5. The sham (top panels; craniotomy only) show no positive staining for occludin or claudin-5. In CCI-TBI (bottom panels) phosphorylated forms of occludin and claudin-5 were clearly evident. The phosphor-specific antibodies used were generated from peptide mapping that identified phosphorylated sites on occludin and claudin-5.
Figure 7B:
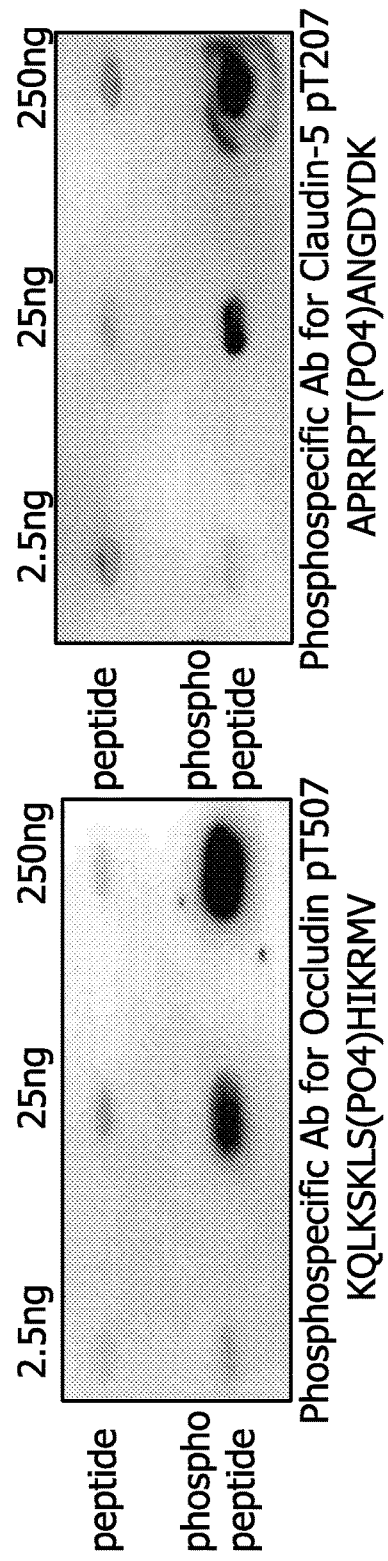
FIG. 7B illustrates dot blots to show antibody specificity. Peptides were applied to a nitrocellulose membrane (pore size, 0.22 pm), using a dot-blot microfiltration manifold unit (Harvard apparatus) attached to infrastructure vacuum (evacuation pressure at 600 mm Hg). Shown in the bottom panel are dot blots demonstrating the specificity of these antibodies to the phosphorylated peptide epitope when compared to the same but unphosphorylated peptide. Peptide sequences are shown below the blot: Occludin pT507 (indicating Threonine 507 of occludin is phosphorylated) (SEQ ID NO:1) and Claudin-5 pT207 (indicating Threonine 207 of claudin-5 is phosphorylated) (SEQ ID NO:2).

Results:

Phosphorylation of TJ proteins has been shown to correlate with altered BBB function. The presence of specific phosphorylation sites for occludin and claudin-5 has been characterized (two TJ proteins abundantly expressed in brain endothelium) (Yamamoti M, Ramirez S H, Sato S, Kiyota T, Cerny R L, Kaibuchi K, et al. *Am J Pathol.* 2008; 172(2): 521-33). Peptide mapping analysis revealed common sites of phosphorylation for occludin and claudin-5 which then allowed us to generate phospho-specific antibodies to these sites (FIG. 7A). Phosphorylated TJ proteins are clearly identified (FIG. 7B). After antigen-affinity column purification, the antibodies are highly specific for the phosphorylated epitope. More importantly in tissue sections from TBI impacted animals, the phosphor-specific antibodies showed areas where TJ proteins were phosphorylated compared to the lack of phosphorylation in the sham control. These results suggest that the subsequent temporal events that occur in TBI induce post-translational modification to the TJs which can lead to BBB compromise.

Example 2. Isolation of Exosomes by Precipitation

Microvesicles/exosomes were isolated from two sources 1) tissue culture media and 2) from blood plasma collected from either experimental TBI animal samples or human samples. Media from BMVEC, D3 and b-End3 cell cultures exposed to different concentrations of various inflammatory mediators was also used. To induce inflammatory insult the following mediators were used: TNFα (50-100 ng/ml; BD Diagnostics, Franklin Lakes, N.J.), IL1β (100 ng/ml, BD Diagnostics), CCL2/MCP-1 (Peprotech Inc, Rocky Hill, N.J.), CCL5/RANTES (Peprotech Inc.), Lipopolysaccharide (LPS) from *Escherichia coli* 0127:B8 (20 ng/ml, Sigma Aldrich, St Louis, Mo.). After exposure endpoint (4 hrs and 24 hrs), collected conditioned media was centrifuged at 3000×g for 15 minutes in order to remove cells and cell debris. For blood samples, blood was allowed to coagulate for 10-15 minutes and then plasma was separated by centrifugation at 10000×g for 10 minutes. Exosomes were isolated using EXOQUICK™ Exosome precipitation solution (System Biosciences, Mountain View, Calif.) according to manufacturer instructions and the pellet was resuspended in equal amount of DDW and kept at −80° C. until use.

Example 3. Isolation of Exosomes by Ultracentrifugation

Exosomes can also be isolated by a series of ultracentrifugations. First the conditioned medium or serum sample (applicable also for CSF) is precleared of cells, dead cells and cellular debris by centrifugation in 50-ml centrifuge tubes for 20 min at 2,000×g in 4° C. The supernatant is then collected and the pellet discarded. In order to minimize contamination, approximately half a centimeter of supernatant is left behind on top of the pellet. The supernatant are then transferred to polyallomer or polycarbonate bottles (appropriate for ultracentrifugation). Next the samples are placed in an ultracentrifuge and spun for 30 min at 10,000×g in 4° C. These supernatants are then transferred to a fresh tube. Caution is taken to ensure that none of the pellet is collected and contaminates the supernatant. At this step the samples are again spun but at higher centrifugation speeds, using at least 70 min at 100,000×g, in 4° C. Note that these high-speed centrifugations require that the tubes be at least three-quarters full (if needed filtered 1×PBS can be added). This resulting pellet contains the exosomes. Therefore the pellet is resuspended in each tube in 1 ml of 1×PBS, using a micropipettor. Of note, there is usually not a visible pellet at this step. For fixed-angle rotors, the pellet is resuspended by flushing up and down the upper side of the tube (towards the bottom) which is where the pellet is located. For swinging-bucket rotors, the bottom of the tube is thoroughly resuspended. In this next final step the isolated exosomes are washed by centrifugation for 1 hr at 100,000×g in 4° C. The supernatant is carefully discarded and the pellet containing a clean exosome fraction is then resuspended in 50 to 100 μl using 1×PBS. The exosomes are then stored for up to 1 year at −80° C. in small aliquots so to avoid repeated freezing and thawing.

Example 4. Identification of the Presence of TJ Proteins on Exosomes Released from Primary Human Brain Microvascular Endothelial Cells The release and profiling of TJ protein-containing exosomes was assessed. Western Blots of purified exosomes from primary human brain microvascular endothelial cells (BMVECs) were conducted.

Figure 8A:
FIG. 8A illustrates Western blots of purified exosomes from primary human brain microvascular endothelial cells (BMVECs). The results from a microvesicle preparation obtained from human BMVECs with or without the inflammatory cytokine TNFα (50 ng/ml) for 24 hrs are shown. NT: not treated. Western blot analysis revealed an increase in the presence of CD63 (exosome marker) and also of occluding (OCC).
Figure 8B:
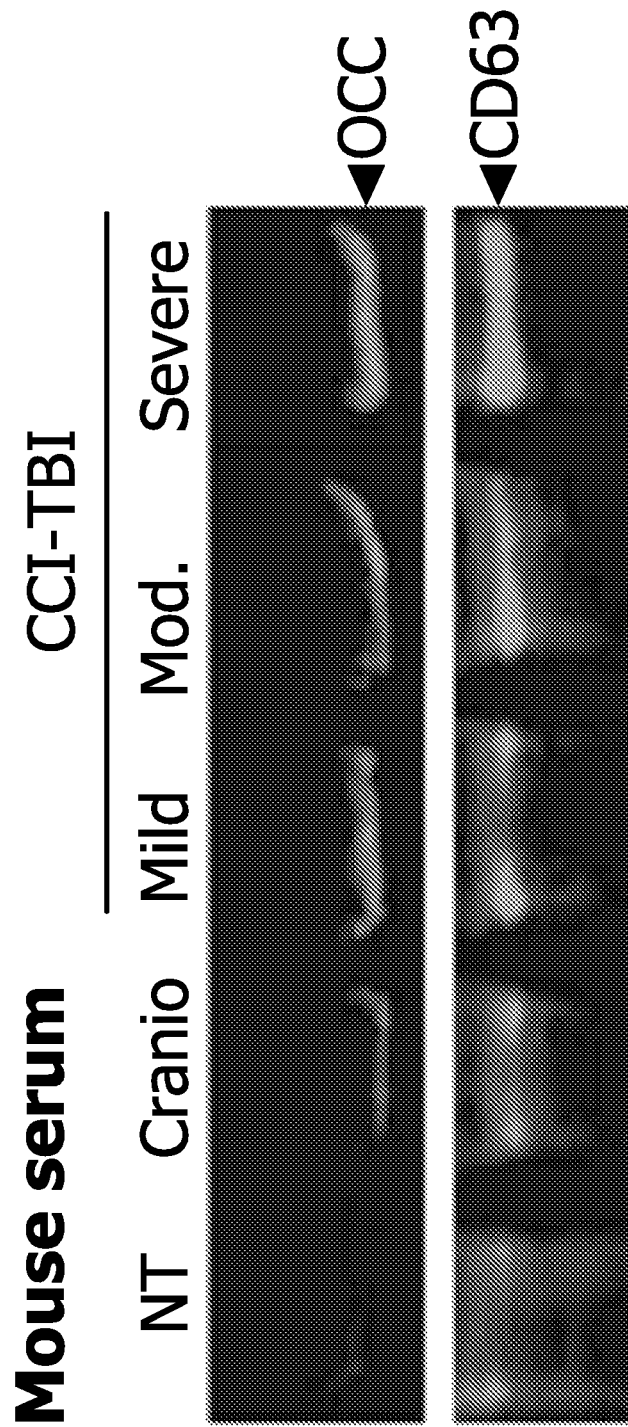
FIG. 8B illustrates Western blots of purified exosomes from mouse serum collected from CCI-TBI (7 days after injury). NT: not treated; Cranio: Craniotomy only control. Similar to the cells in culture, the injured brain endothelium released detectable amounts of CD63 and occludin. These were the first results that indicated that brain endothelial cells release exosomes with TJ proteins post TBI.

Exosomes were isolated and enriched from media of primary human Brain Microvascular Endothelial Cells (BMVEC) exposed to inflammatory insult with 50 ng/ml TNFα for 24 hours. Microvessels isolated from the resection path of patients that underwent surgical removal of intractable epileptogenic cerebral cortex have provided a well defined endothelial source for reconstituting an in vitro BBB model (Ramirez S H, Fan S, Dykstra H, Reichenbach N, Del Valle L, Potula R, et al. *J Neurosci*. 2010; 30(28): 9454-64; Ramirez S H, Heilman D, Morsey B, Potula R, Haorah J, Persidsky Y. *J Immunol*. 2008; 180(3): 1854-65). In TBI the brain endothelium is under severe inflammatory insult. Western Blots were carried out as follows.
Western Blotting SDS-PAGE and Western blot analysis was performed as previously described (Ramirez S E, Potula R, Fan S, Eidem T, Papugani A, Reichenbach N, et al. *J Cereb Blood Flow Metab*. 2009; 29(12):1933-45). Exosomes isolated as described in Example 2 were resuspended with 6× loading buffer containing DTT and then boiled for 10 min at 95° C. The proteins in the exosomes were then separated by SDS-PAGE (4-20% precast gels) (Thermo Scientific), followed by electrophoretic transfer to nitrocellulose membranes. The primary antibodies were diluted in 1×TBS/0.1% Tween 20 and used to detect CD63 (antibody diluted 1:200, Santa Cruz Biotech), and occludin (antibody diluted 1:300, Invitrogen). All primary antibodies were incubated with the membranes overnight at 4° C. with gentle shaking. For detection, species-specific secondary antibodies conjugated to IRDye680 and IRDye800CW (diluted 1:1000) (Thermo Scientific) were added to the membranes for 1 hr at room temperature. Fluorescent signals were detected and quantitated using a LI-COR ODYSSEY® (Lincoln, Nebr.) imaging system.
Results:

BMVECs shed a low amount of detectable exosomes as indicated by Western Blot using an antibody to the exosome marker CD63 (FIG. 8 A). The results also showed the presence of occludin in these exosome preparations, as indicated by Western Blot using an antibody to occludin (FIG. 8 A). In addition, inflammatory stimuli (TNFα) induced a marked increase in the release of exosomes containing occludin. Taken together these results point to an active process of exosome shedding by brain endothelium cells which is significantly upregulated when inflammatory insult is present.

Example 5. Detection of Exosome Containing TJ Proteins in Peripheral Blood from Mice by an ELISA-Based Diagnostic Blood Test for TBI This study demonstrates that an assay for TJ proteins on exosomes can accurately determine the presence of a brain injury in the subject under study.
Western Blots Using the CCI-TBI model, blood samples from mice in the following groups were analyzed: craniotomy only, TBI mild (1.5 m/s), TBI moderate (3.5 m/s) and TBI severe (5 m/s). After exosome isolation from blood serum, the detection of CD63 by Western Blot (antibodies to CD63 were diluted 1:200, Santa Cruz Biotech) was seen in all experimental groups which increased as a function of TBI severity (FIG. 8 B). Antibodies to occludin (1:300, Invitrogen) detected a marked increase in occludin protein in blood samples from TBI animals. These findings and those of Example 4 demonstrate that brain endothelial cells (human or mouse) release great amounts of exosomes which contain one of the key tight junction proteins found at the BBB.
MSD ELISA Preparation Peripheral blood samples from mice were tested for the presence of exosomes containing occludin. ELISAs were established using the ELISA development kits from MSD® (Meso Scale Discovery. Gaithersburg, Md.) using commercially available reagents to provide an ELISA-based diagnostic blood test for TBI, as follows. The MSD® ELISA kit methodology provides higher sensitivity and dynamic range compared to other ELISA systems (Gowan S M, Hardcastle A, Hallsworth A E, Valenti M R, Hunter L J, de Haven Brandon A K, et al. *Assay Drug Dev Technol*. 2007; 5(3): 391-401; Fu Q, Zhu J, Van Eyk J E. *Clin Chem* 2010; 56(2): 314-8). Compared to traditional ELISA which uses enzymes such as horse radish peroxidase or alkaline phosphatase as signal generators, MSD® uses SULFO-TAG™ labels containing ruthenium (II) tris-bipyridine NHS ester Ru(bpy)$_3^{2+}$ to generate light, providing ultra-low detection limits and up to five logs of linear dynamic range.

Multiwell plates from MSD® were coated with exosomes isolated from cell culture or from blood, for 30 min at room temperature with coating buffer (Meso Scale Discovery, Gaithersburg, Md.). The wells were washed and blocked with MSD® blocking solution, containing 5% BSA in PBS. Primary antibodies diluted in 1×PBS/0.1% Tween 20 were used to detect exosome protein markers and TJ proteins. All antibodies were incubated for 1 hour at room temperature under gentle shaking. Bound primary antibodies were exposed to the corresponding species-specific MSD® SULFO-TAG™ secondary antibodies (1 u/ml, Meso Scale Discovery, Gaithersburg, Md.) for 1 hour at room temperature under gentle shaking, followed by detection using the SECTOR® Imager 2400 MSD. Data analysis was performed using the MSD® DISCOVERY WORKBENCH® Software.
Stable Overexpression of Occludin and Claudin-5 in HEK 293 Cells.

Figure 9A:
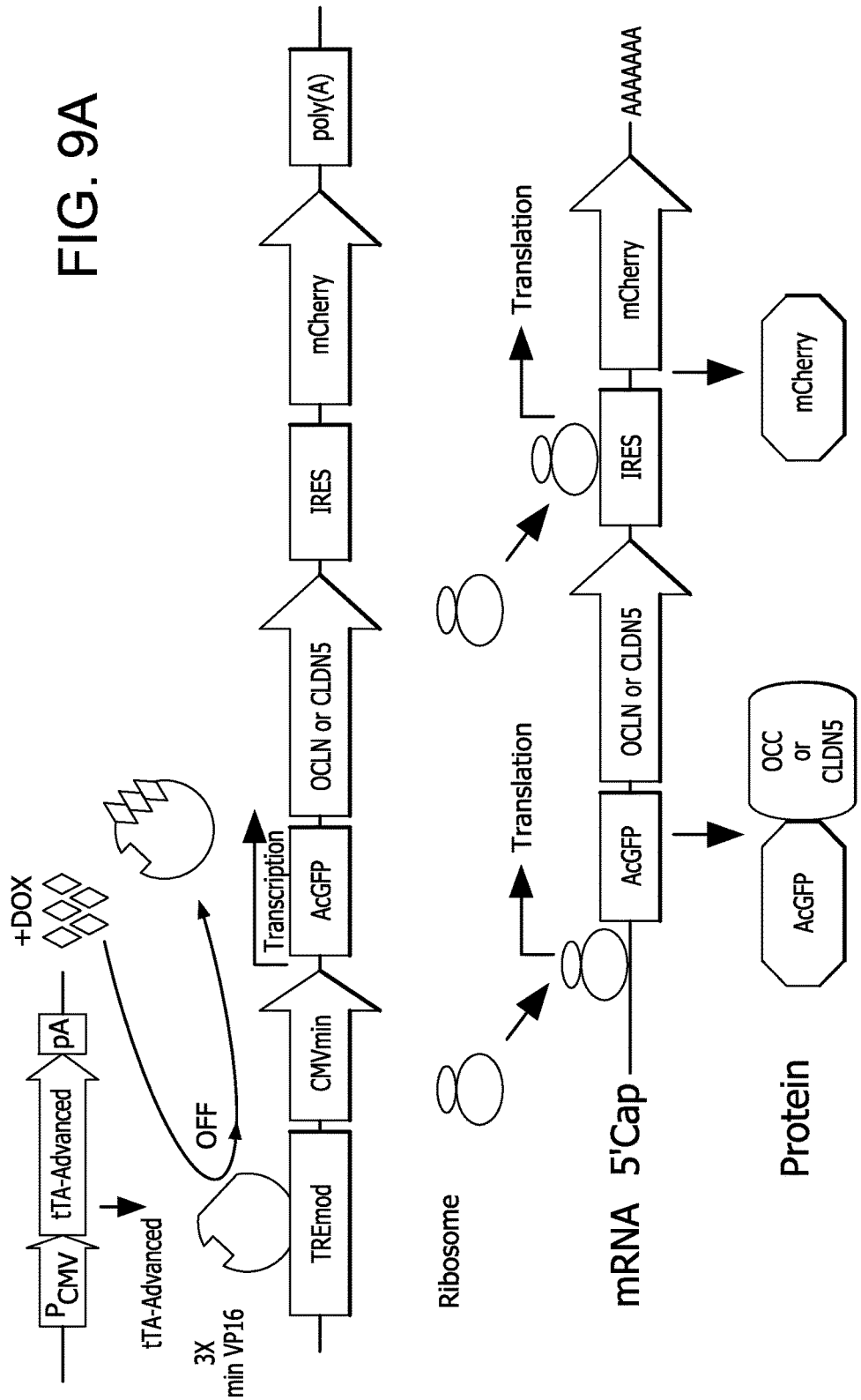
FIG. 9A illustrates a schematic diagram of an inducible expression system for occludin and claudin-5. The system is designed to use reporter constructs that express bicistronic mRNA under the control of a tetracycline inducible promoter (tetracycline response element "TRE"). The first cassette expresses the fusion protein of AcGFP with human claudin-5 or occludin at the N-terminus. The second cassette expresses mCherry red fluorescence protein after an internal ribosome entry site (IRES). In the induced state, the Tet-transactivator protein (tTA) activates transcription by binding to the TRE element. In the uninduced state, the addition of doxycycline (Dox) prevents the tTA protein from binding to the TRE promoter region, thereby blocking transcription.

An in vitro model was developed for the production of exosomes expressing occluding and claudin-5, for use in optimizing the MSD® ELISA before employing it for testing peripheral blood samples. Molecular cloning techniques were employed to overexpress the human genes of occludin and claudin-5 in a cell line that lacks tight junctions. This was necessary since BMVECs are not always available due to the length of time required to culture the cells and the limited number of passages before the cells undergo senescence. Open reading frames for the full length human cDNA of occludin and claudin-5 were acquired from ORIGENE™ Technologies Inc (Rockville, Md.). The cDNA was then cloned into a TET-OFF® Advanced Inducible Gene Expression System (Clontech, Mountain View, Calif.). The system is designed to use reporter constructs which express the bicistronic mRNA under the control of an inducible promoter. The reporter construct contains two expression cassettes from one mRNA transcript. The first cassette expresses the fusion protein of human claudin-5 or occludin with an AcGFP tag at its N-terminal, and the second cassette expresses the mCherry protein after the IRES (Internal Ribosome Entry Site) (FIG. 9A). In the TET-OFF® system, the un-induced basal state is maintained in the presence of doxycycline (Dox), which prevents the Tet-Advanced transactivator protein from binding to the TRE promoter region and inducing high-level transcription. For stable expression the constructs were transfected using Lipofectamine LTX (Invitrogen) into the HEK293 cell line. HEK293 cells (purchased from the ATCC) were grown in DMEM (Invitrogen) supplemented with 10% FBS (Invitrogen). Since the constructs also contain the resistance gene for neomycin, stably transfected cells were isolated following neomycin selection (Geneticin, Life Technologies, Inc.).

Figure 9C:
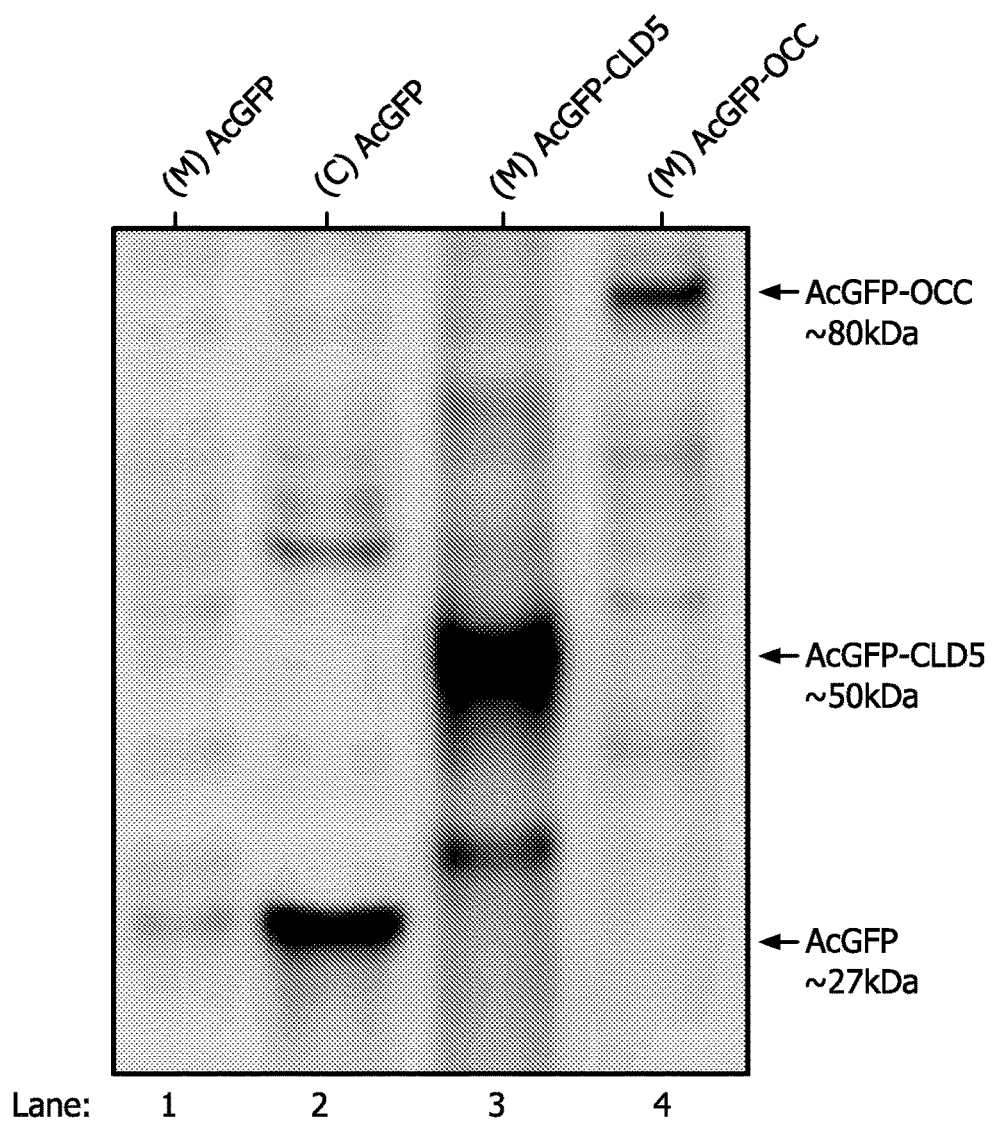
FIG. 9B illustrates overexpression of occludin and claudin-5 in HEK293 cells. Representative images from HEK293 cells transfected with the tight junction protein expressing constructs are shown. The top left panel shows the cytosolic expression of unfused AcGFP. The middle and lower left panels show the membranous expression of unfused AcGFP. The middle and lower left panels show the membranous expression of AcGFP-CLD5 and AcGFP-OCC, respectively. The cytosolic expression of mCherry is shown for all constructs (middle column). Original objective magnification was 20× and 60× (insert). Note the presence of tight junctions (arrows).
FIG. 9 C illustrates Western blots probed for GFP showing the expression of the fused tight junction proteins AcGFP-CLD5 and AcGFP-OCC without doxycycline (Dox, 200 ng/ml) for 48 hr in HEK293 cells.
Figure 9D:
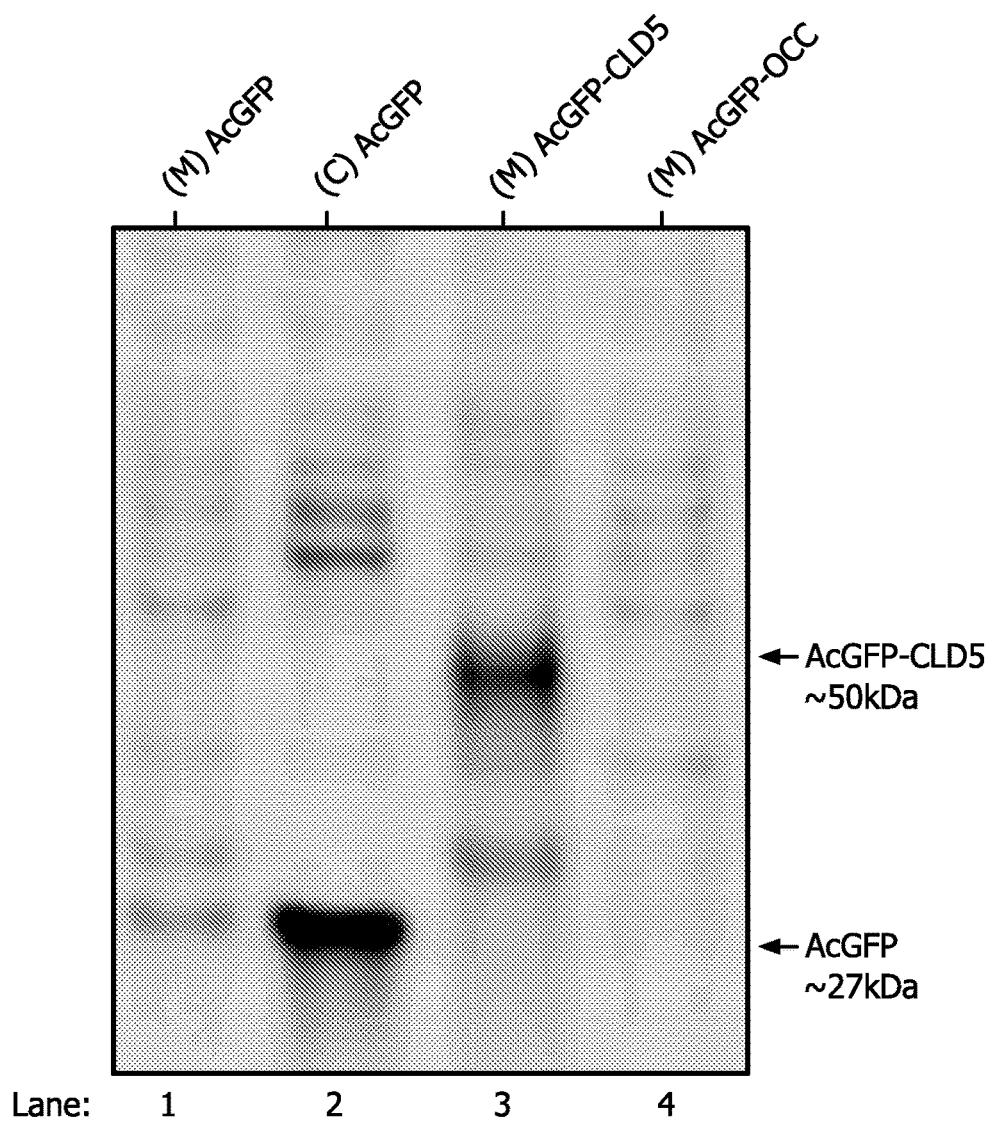

When in the induced state, both mCherry and AcGFP-CLD5 or -OCC are produced at a constant ratio because the expression originates from the same mRNA. Addition of Dox halts transactivation and allows protein turnover to be monitored as a function of time. Since cell lines are known for shedding high levels of exosomes, HEK293 cells were chosen and transfected with the inducible constructs for expression of either AcGFP, AcGFP-CLD5 or AcGFP-OCC (FIG. 9B) and visualized after 24 hrs. As expected, transfection with the vector coding for unfused AcGFP caused accumulation of AcGFP in the cytosolic compartment (FIG. 9B, top panel). The reference reporter, mCherry, also appeared in the cytosol. However, transfection with vectors that express the AcGFP-CLD5 or AcGFP-OCC localized the tethered tight-junction protein to the membrane (FIG. 9B, middle and bottom panel, respectively). To confirm transgene regulation, transfected cells with or without the addition of Dox were lysed after 48 hr and then evaluated by Western Blots against AcGFP using an anti-AcGFP antibody (1:1000 dilution, Clontech, Mountain View, Calif.) (FIG. 9C). Western Blots were conducted as described in Example 5. Fractions from cells without Dox show protein expression from the three transgenes having the corresponding molecular weights for the AcGFP unfused and fused TJ proteins. As visualized by microscopy, only the AcGFP fused to the TJ protein appears in the membrane fractions; (M) indicates membranous and (C) indicates cytosolic (FIG. 9C). Exposing the cells to 200 ng/ml of Dox turns off gene expression and thus a significant decrease in the fused TJ protein is observed (FIG. 9D). As can be seen in the immunoblot, no significant reduction in the unfused AcGFP was noted when Dox was present (FIG. 9D) which demonstrates that AcGFP has slow turnover kinetics affected only when fused to the TJ protein. Next, we examined microvesicle production from the transfected HEK293 was examined.

Exosome Analysis by Flow Cytometry

Individual exosomes were further isolated from transfected HEK293 cells by cell sorting flow cytometry as follows. Exosomes isolated (as indicated above) from transfected HEK293 expressing either GFP only, GFP-occludin- or GFP-claudin-5 were dissolved in flow bufer (1% BSA in PBS), and analysed using the MACSQuant 10 analyser (Miltenyi Biotech, Germany). Plots were generated using FlowJo Software, Tree Star, Inc. (Ashland, Oreg.).

Figure 10:
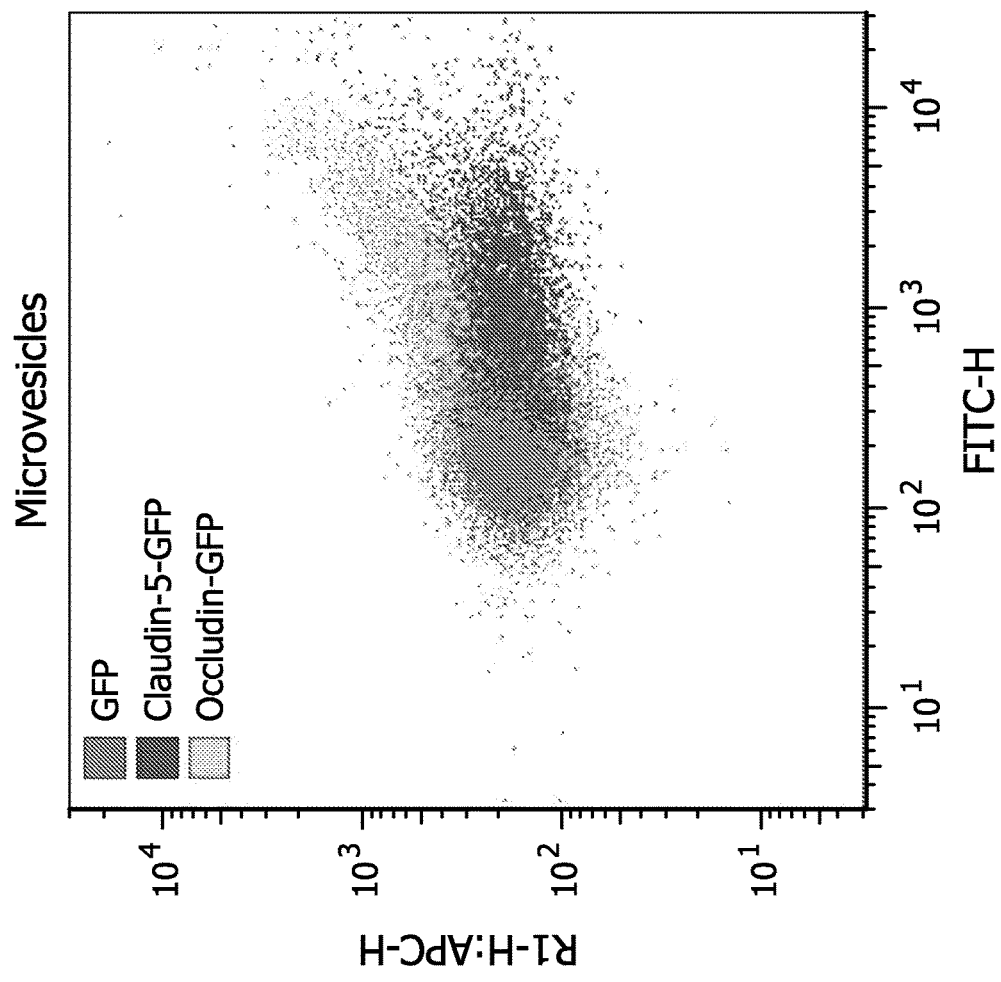
FIG. 10 illustrates the detection of extracellular microvesicles by flow cytometry. Isolated microvesicles/exosomes (As in Example 2) from transfected HEK293 cells expressing either the GFP only, GFP-occludin or GFP-claudin-5 overexpressing constructs were dissolved in flow buffer (1% BSA in PBS) and analyzed by a MACSQuant 10 analyser. Dot plots were generated using FlowJo Software. These TJ containing exosomes from transfected HEK293 cells were used for the development of the MSD ELISAs that follow.

FIG. 10 shows the combined results of flow cytometry from microvesicle preparations of HEK293 expressing AcGFP, AcGFP-OCC and AcGFP-CLD5. The dot plot shows the abundant amount of microvesicles expressing the GFP reporter that are shed by these cells. Therefore the microvesicles released from the stably expressing occludin and claudin-5 cell lines (FIG. 9A-D) provided ample sample for calibration, threshold determination and optimization of the MSD ELISA.

Analysis of Peripheral Blood Samples from Mice by MSD ELISA

Figure 11A:
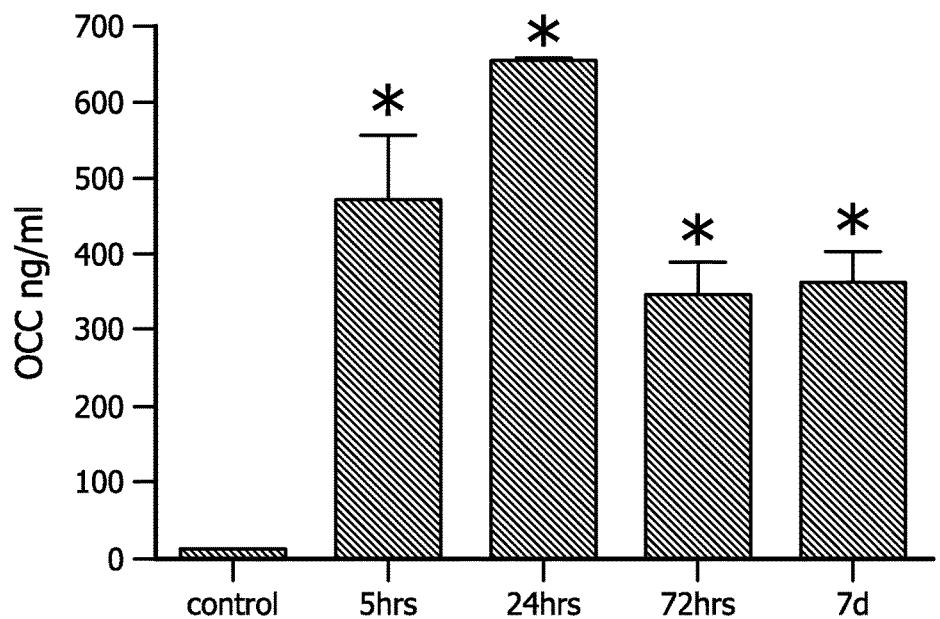
FIGS. 11 A and 11 B illustrate the detection of TJ protein in exosomes from impacted animals using MSD ELISA. Use of the MSD ELISA platform for the rapid detection of shed BBB TJ proteins in serum is shown. After isolation of exosomes, the samples were run in the MSD ELISAs for CD63 and occludin.

MSD® ELISA was performed with exosomes isolated from the blood of impacted animals. After isolation of exosomes, the samples were run in the MSD® ELISA described above for CD63 and occludin. FIG. 11A shows a time course for the amount of occludin (OCC)/exosome in serum after moderate CCI-TBI. The results from the assay showed a significant presence of TJ protein increase that was also sustained over time. Although high levels of exosomes/TJs appeared at all time points after the injury, it appeared that peak exosome release occurred at 24 hrs.

Figure 11B:
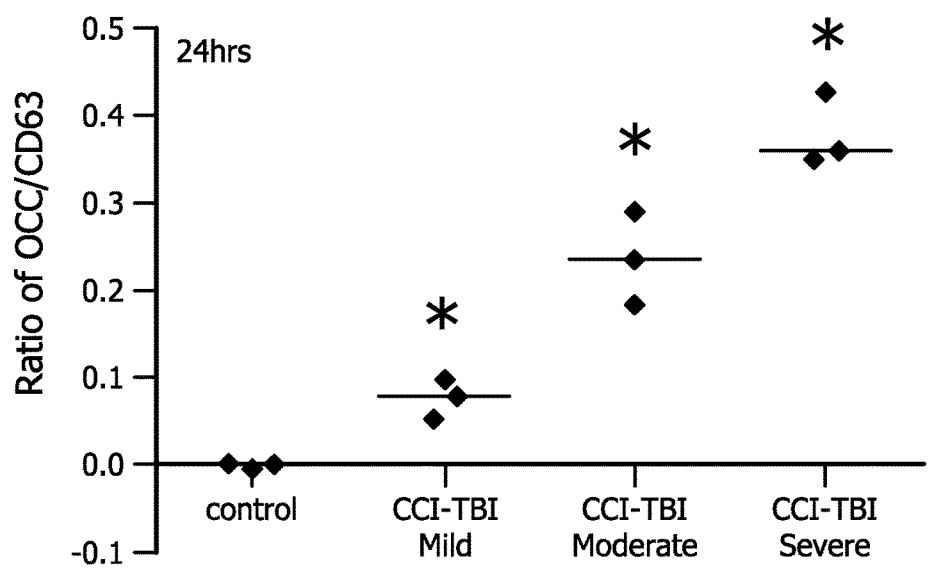

Peripheral blood from animals which had been suffered TBIs of varying severity and control animals was used to isolate exosomes. The samples were then run in the MSD® ELISA for CD63 and occludin. To normalize the results, the amount of occludin detected was divided by the amount of CD63 detected by the assay for each sample. The results are shown in FIG. 11B as the mean±SEM (n=3). Differences between the various severities of CCI-TBI at 24 hours after injury may be clearly seen. The graph shows how the ratio of OCC/CD63 increases with the severity of the injury.

The results demonstrate that 1) exosomes containing TJs are released from the endothelium following neurotrauma, and 2) the release can be detected by assay for the presence of the exosome TJ proteins.

Example 6. Measurement of TJ-Containing Exosomes in Human Serum by ELISA to Evaluate Brain Injury in Human Patients The following study demonstrates that the provided assay can accurately indicate the differences in injury using blood samples from patients exposed to different TBI severity. A recently reported TBI study was used for this assessment (Blyth B, Farahvar A, He H, Nayak A, Yang C, Shaw G, et al. *J Neurotrauma*. 2011).

Figure 12:
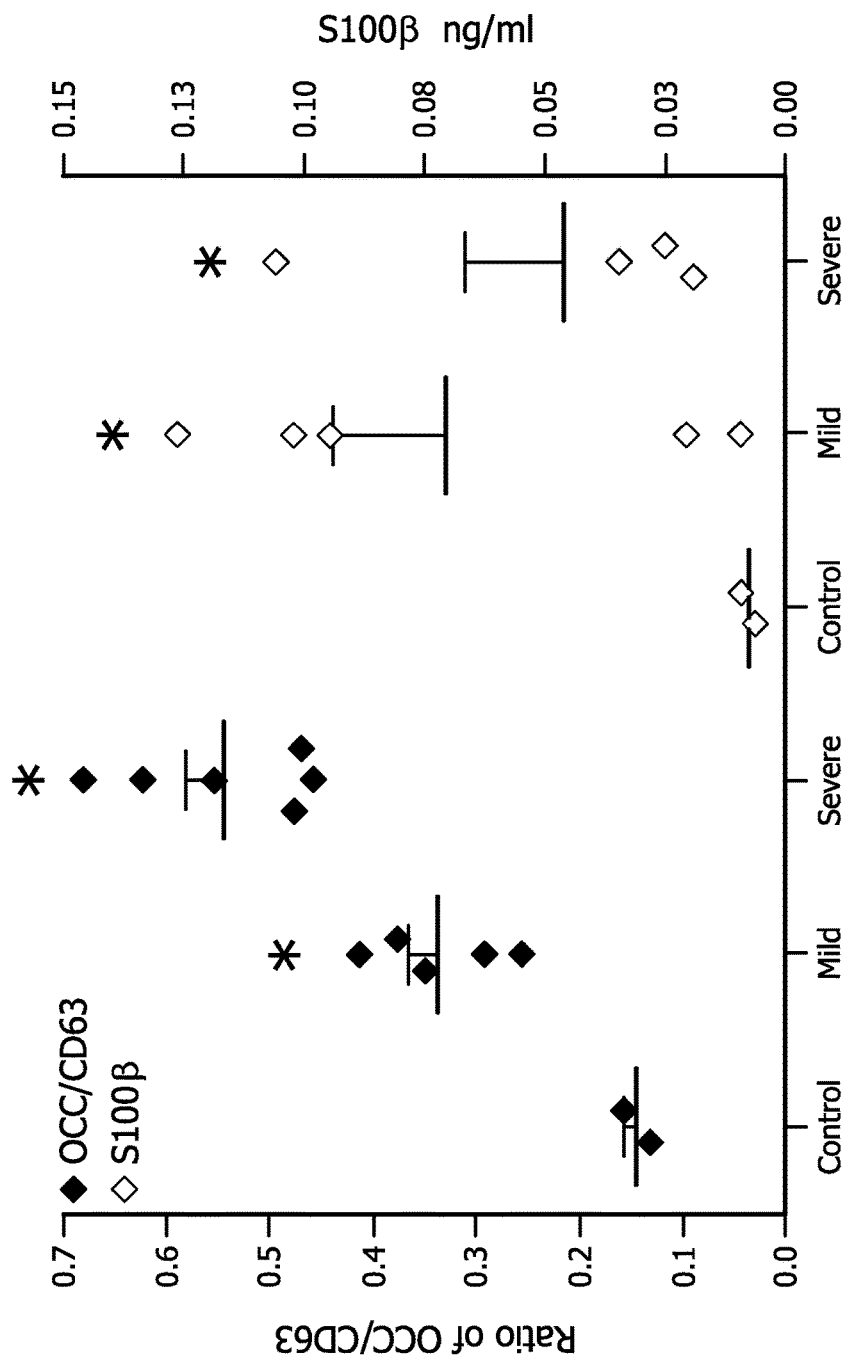
FIG. 12 illustrates the MSD ELISA detection of TJ protein in exosomes from serum of patients exposed to TBI. The MSD ELISA shows differences between no injury and injury and between mild to severe TBI (based on GCS scores), as shown by the ratio of OCC/CD63 (left axis). For comparison, the right axis shows the values for S100β determined by ELISA. The results for S100β show changes from normal controls and individuals with TBI but did not differentiate between the different injury levels of TBI. The results are shown as the mean±SD, * denotes a difference of P<0.05 between the TBI groups and the non-TBI normal control.

Human serum or CSF samples from individuals who have experienced TBI were provided as part of collaboration with Dr. Brian Blyth and Dr. Jeffrey Bazarian at the University of Rochester Medical Center. The MSD ELISA as described in Example 5 was used to test samples from individuals that suffered mild, moderate and severe TBI (based on Glasgow Coma Scale scores). Serum from the patients was used to isolate exosomes. The samples were then assayed by MSD ELISA for CD63 and occludin. To normalize the results, the amount of occludin detected was divided by the amount of CD63 detected by the assay for each sample. Although the sample number is low, distinctions were clearly evident between no TBI, mild and severe TBI (FIG. 12). For comparison, S100β levels (a candidate biomarker for brain injury) was also measured (right axis). The results suggest that both assays (OCC/CD63 and S100β) can differentiate between injury and non-injury. However unlike the assay for S100β, the assay of the invention was able to distinguish between the severity of the injury in the amount of exosomes present (using exosome markers) and TJ protein content. The results presented here, demonstrate that a sensitive ELISA was developed to detect TJ proteins shed from the BBB after head injury in humans.

Example 7. BMVECs Shed Extracellular Microvesicles

Figure 13:
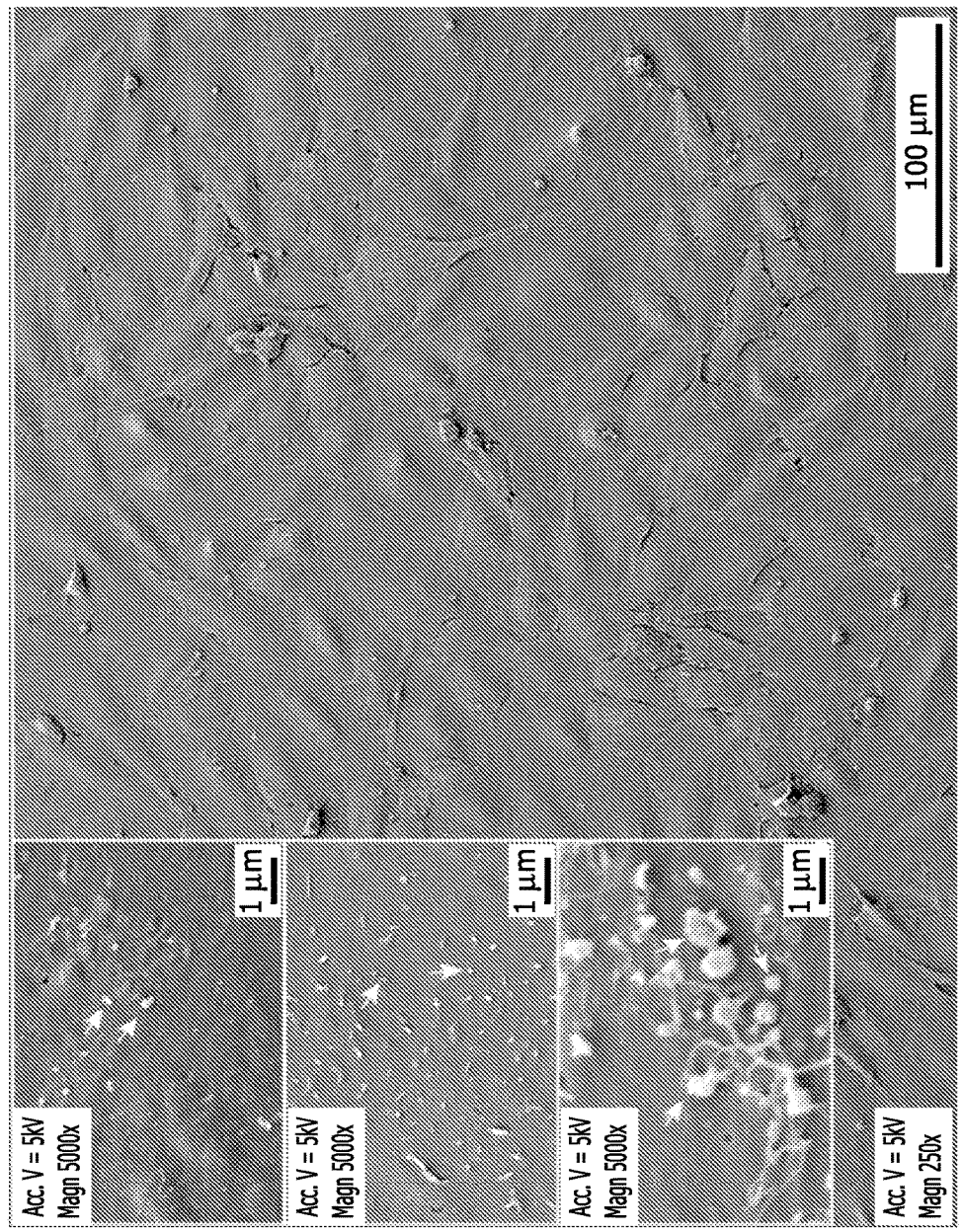
FIG. 13 illustrates scanning electron micrographs (SEM) of extracellular microvesicles (which include exosomes) released from BMVECs exposed to TNFα (100 ng/ml) for 24 hours. Arrows in the inserted images show extracellular microvesicles ranging in size from 0.2 to 1.1 micron in diameter.
Figure 14A:
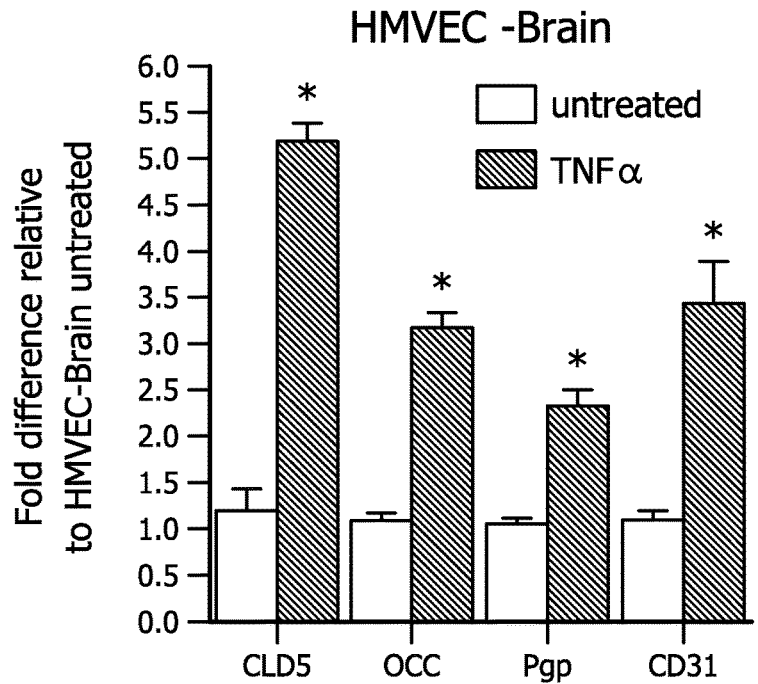
FIGS. 14A to 14D illustrate a comparative analysis of exosomes/microvesicles isolated from untreated and TNFα-treated cultures of primary human brain (FIG. 14A), lung (FIG. 14B), dermal (FIG. 14C) and coronary (FIG. 14D) endothelial cells. This figure denotes that shed TJPs are detected only in brain endothelial cells, when the exosomes/microvesicles are captured by either P-glycoprotein (Pgp) or BCRP, using MSD ELISA. The results are shown as the mean SD, * denotes a difference of P<0.05.
Figure 14B:
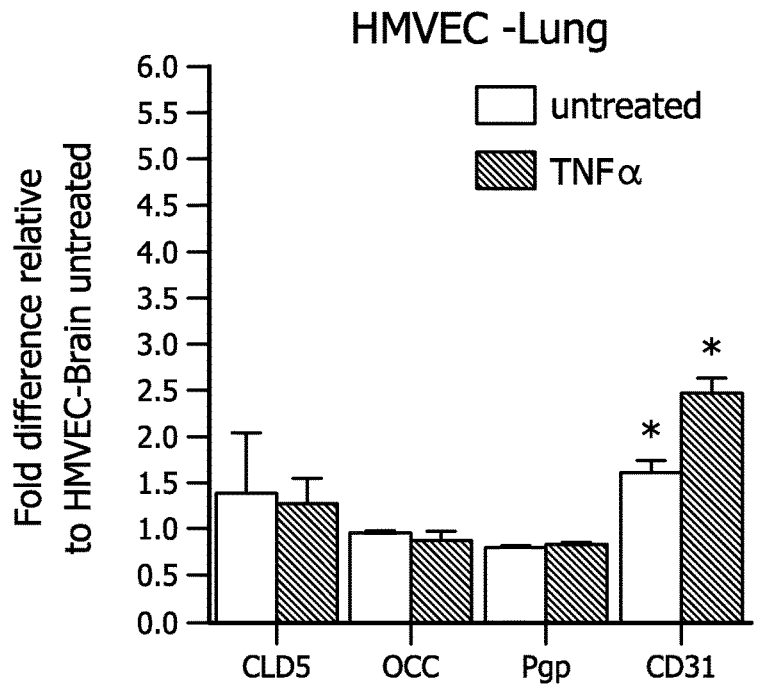
Figure 14C:
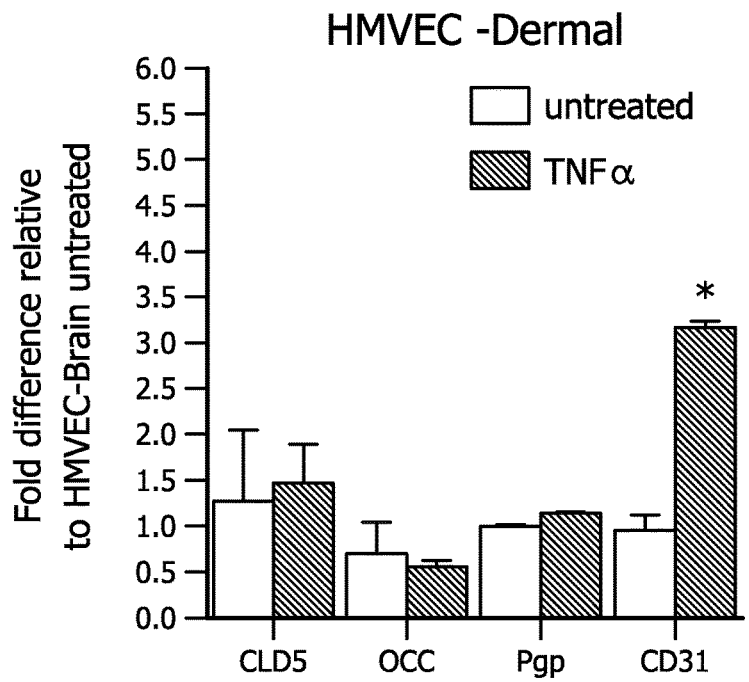
Figure 14D:
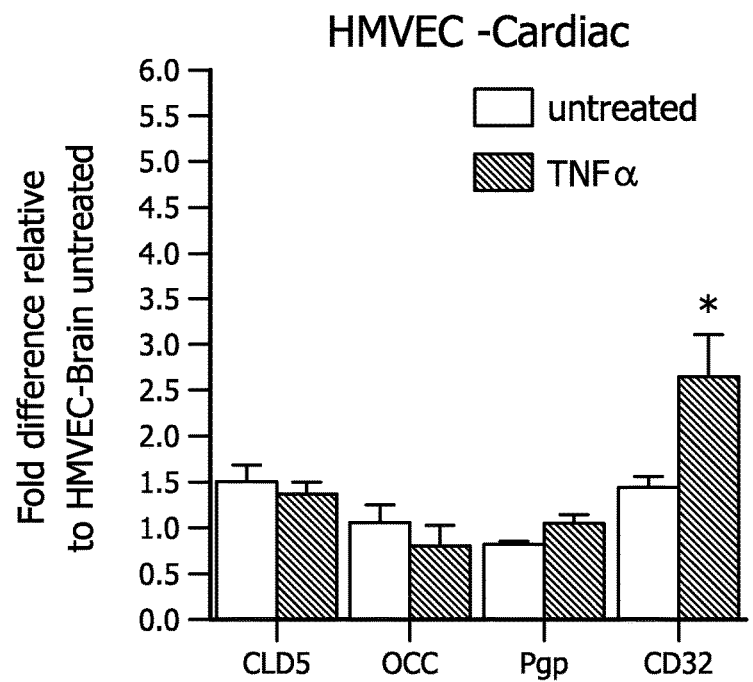

The following experiment demonstrates that brain microvascular endothelial cells (BMVEC) produce extracellular microvesicles after stimulation with TNFα, which is one of the main cytokines that is present during inflammation of the brain. This experiment shows that cytokines produced during injury can cause remodeling of the brain endothelium, which activates the cells and induces the shedding of extracellular microvesicles. BMVECs were isolated as previously described (Bernas M J, Cardoso F L, Daley S K, Weinand M E, Campos A R, Ferreira A J, et al. *Nat Protoc.* 2010, 5(7):1265-1272). Human BMVEC were cultured from brain tissue recovered from the resection path prior to removal of epileptogenic material during surgical treatment of epilepsy (performed by Dr. Martin Weinand, Neurosurgery, University of Arizona HSC, Tucson, Ariz.). BMVECs of low passages and from different donors were used in repeated experiments. BMVECs were exposed to 100 ng/ml of TNFα for 24 hours. The cells were rinsed and then fixed with 2.5% glutaraldehyde in PBS, treated with 1% tannic acid and 1% OsO4, and dehydrated with a graded ethanol series. Cells were then processed for scanning electron microscopy at the UPENN cell morphology core. The results are shown in FIG. 13. As indicated by the arrows in the inserted images, microvesicles can be seen budding on the surface of BMVECs activated with TNFα.

Example 8. Improved Specificity of MSD ELISA for Occludin Detection in Microvesicles/Exosomes by Capture with Antibodies to P-Glycoprotein The MSD® ELISA described in Example 5 was slightly modified. Multiwell plates from MSD® (Meso Scale Discovery, Gaithersburg, Md.) were coated with capture antibodies to P-glycoprotein (Pgp) for 30 minutes at room temperature with coating buffer (MSD). The wells were washed and blocked with MSD blocking solution containing 5% BSA in PBS. Primary antibodies to occludin diluted in 1×PBS/0.1% Tween 20 were used to detect the target TJP. All antibodies were incubated for 1 hour at room temperature under gentle shaking. Bound primary antibodies (not the capturing antibodies) were exposed to the corresponding species-specific MSD® SULFO-TAG™ secondary antibodies (1 µg/ml) for 1 hr at room temperature under gentle shaking, followed by detection using the SECTOR® Imager 2400 (MSD®). Data analysis was performed using MSD® DISCOVERY WORKBENCH® Software. As can be seen in FIG. 14A-D, the use of Pgp capture enhances the specificity of the assay. Primary human endothelial cells from dermal, cardiac (coronary endothelial), lung and brain were stimulated with TNFα (100 ng/ml for 24 hours) followed by microvesicle isolation as described above. As shown in FIG. 14A-D, only brain endothelial cell microvesicles/exosomes had high levels of detectable TJ proteins occludin and claudin-5. Of note, Pgp is highly enriched in brain endothelium.

Figure 15:
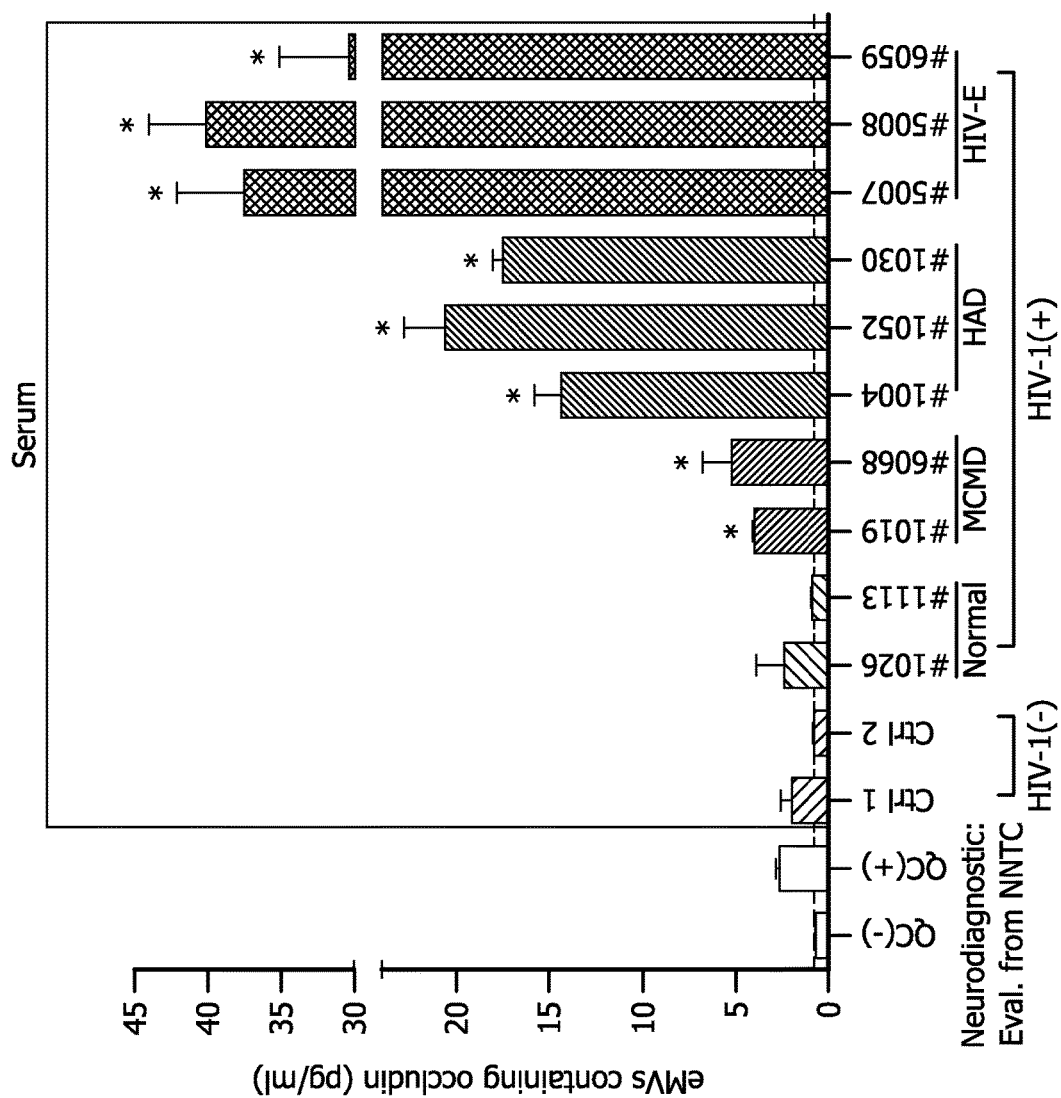
FIG. 15 illustrates the detection by MSD ELISA of TJPs in exosomes from the serum of patients infected with HIV-1 and diagnosed with various degrees of neurocognitive deficit: minor cognitive motor deficit, MCMD; HIV-associated dementia, HAD; and HIV encephalopathy, HIV-E (samples were obtained from The National NeuroAIDS Tissue Consortium (NNTC)). The samples were collected on or within days of neurodiagnostic evaluation. The analyses were performed using MSD ELISA for occludin, which showed a graded difference in the amount of occludin-containing microvesicles/exosomes (eMV) isolated from patients when comparing the various HIV-1 related neurocognitive deficits which reflect injuries to the brain. The results are shown as the mean±SD. * denotes a difference of P<0.05 of comparison with normal (non-HIV) control.

Example 9. Increased Levels of Occludin in Microvesicles/Exosomes in the Serum of HIV+ Patients Diagnosed with Neurocognitive Impairment Caused by Injury to the Brain as a Result of the HIV Infection The MSD ELISA assay for occludin in microvesicles/exosomes was used to test blood samples from HIV-1 infected individuals having an injury to the brain related to the HIV infection with resulting neurocognitive impairment. Clinical samples obtained from the National NeuroAIDS Tissue Consortium (NNTC) were processed for microvesicle/exosome purification as described above. Samples were received from the NNTC, with the criteria that the samples be grouped into: HIV+ with normal neurological score, HIV+ with suspected minor cognitive motor deficit (MCMD), HIV+ with suspected HIV associated dementia (HAD) and HIV+ with HIV-encephalitis (HIV-E). As shown in FIG. 15, analysis with the MSD ELISA for occludin showed a graded difference in the amount of occludin-containing microvesicles/exosomes isolated from patients when comparing the various HIV-1 related encephalopathies which are examples of injuries to the brain. These results demonstrate that microvesicles/exosomes derived from the BBB can be used as a measure of neurovascular injury that is directly proportional to neurocognitive status.

Figure 16:
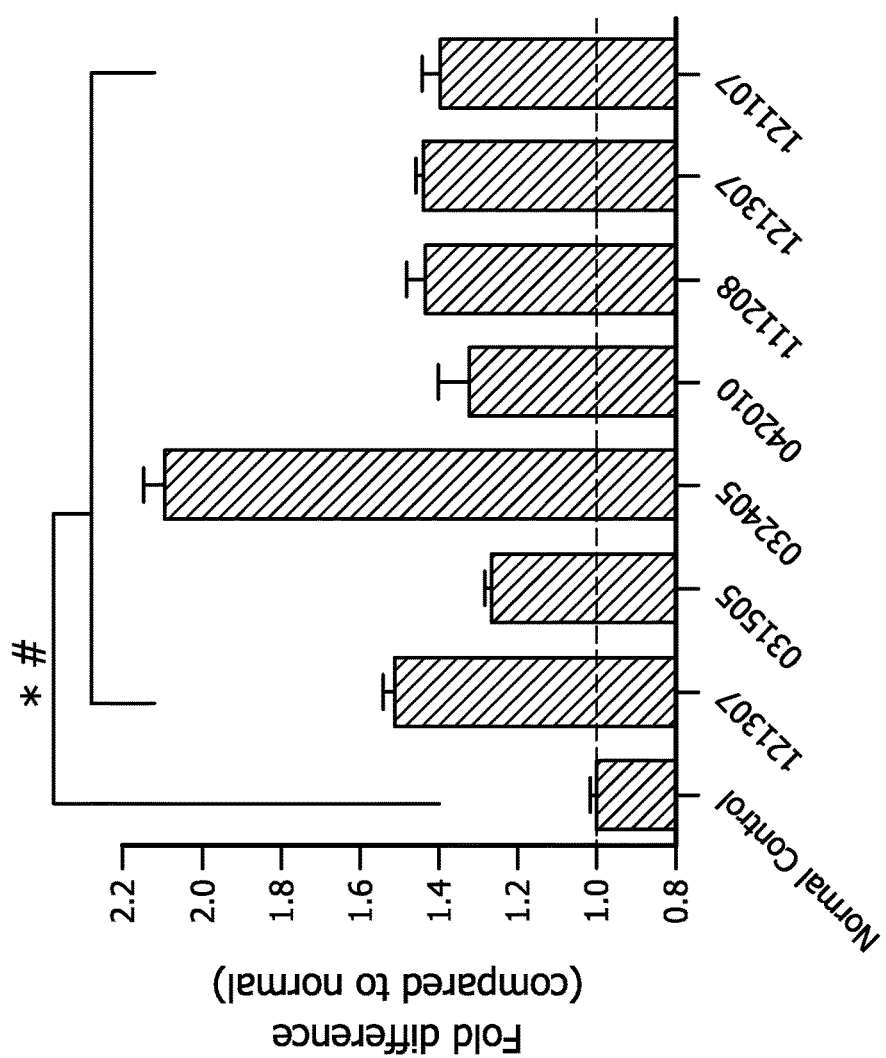
FIG. 16 illustrates occludin presence on exosomes isolated from serum samples of a normal individual and from epileptic cases acquired from the University of Arizona Health Center. The normal control is from a serum sample from an individual with no known history of epilepsy. Occludin presence was clearly increased in microvesicles/exosomes isolated from serum samples from epileptic cases, compared with the normal control. The data shown has been converted to the "fold change" which is derived from the raw value ratio of the epileptic case to the non-epileptic control. For each case, exosomes were isolated, loaded on to the MSD ELISA and read three individual times. Averages were plotted along with SD. * indicates P<0.01. Statistical determinations were done using 1 way ANOVA with Dunnett's post hoc test.

Example 10. MSD ELISA for Occludin Indicates Neurovascular Dysfunction in Patients with Epilepsy Clinical samples were obtained from the University of Arizona (neurosurgery department) and processed for microvesicle/exosome purification as described above. Occludin presence was clearly increased on microvesicles/exosomes isolated from serum samples from epileptic cases, compared to the normal control from a serum sample from an individual with no known history of epilepsy. The data shown in FIG. 16 has been converted to "fold change" which is derived from the raw value ratio of the epileptic case to the non-epileptic control.

All references herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should also be made to the appended claims, rather than to the foregoing specification, as indicating the scope of the invention.

What is claimed is:

1. A method comprising:
   a) capturing exosomes from a test sample from a subject, the sample comprising blood, blood plasma, blood serum, cerebrospinal fluid or urine, by contacting the sample with antibody to P-glycoprotein;
   b) determining the level of a tight junction (TJ) protein in the captured exosomes, wherein said TJ protein is occludin, claudin-3, claudin-5, claudin-12, Zonula Occludens-2, Zonula Occludens-3, junctional adhesion molecule-A, junctional adhesion molecule-B or junctional adhesion molecule-C, or any combination thereof; and
   c) comparing the level of said TJ protein in said exosomes captured from said test sample to the level of the TJ protein in a control; and
   d) determining an elevated level of the TJ protein in said exosomes captured from said test sample relative to the level of the TJ protein in said control, thereby indicating that the subject has sustained an injury to the brain; and
   e) administering to the subject a treatment for a disorder or condition associated with said injury to the brain.

2. The method of claim 1 further comprising conducting a diagnostic procedure on the subject comprising computed tomography (CT) scanning, magnetic resonance imaging (MRI), X-ray imaging, blood tests, physical examination, cognitive testing, electroencephalography, neuromonitoring, intracranial pressure (ICP) monitoring, assessing cerebral perfusion pressure (CPP) or determining the subject's Glasgow coma scale score (GCS).

3. The method of claim 2 wherein said neuromonitoring comprises jugular venous oximetry, brain tissue oxygen tension monitoring, cerebral microdialysis or thermal diffusion flowmetry.

4. The method of claim 1 wherein said treatment comprises surgical treatment, head elevation, osmotic therapy, hyperventilation, debridement, optimizing venous drainage, cerebrospinal fluid (CSF) drainage, sedation, temperature management, glucose management, administering an antiepileptic drug or administering a neuroprotective agent.

5. The method of claim 4 wherein said CSF drainage comprises the use of a ventricular catheter.

6. The method of claim 4 wherein said optimizing venous drainage comprises keeping the head of the subject in neutral position.

7. The method of claim 4 wherein said osmotic therapy comprises the administration of mannitol or hypertonic saline.

8. The method of claim 4 wherein said sedation comprises the administration of a barbiturate, propofol, a benzodiazepine or an opiate.

9. The method of claim 4 wherein said antiepileptic drug is phenytoin or valproic acid.

10. The method of claim 4 wherein said neuroprotective treatment comprises the administration to the subject of progesterone, magnesium, citicoline, cyclosporine or erythropoietin.

11. The method of claim 4 wherein the TJ protein is selected from the group consisting of occludin, claudin-5, and the combination thereof.

12. The method according to claim 1 wherein the level of TJ protein in exosomes from the test sample is determined by enzyme-linked immunosorbent assays utilizing a label which emits light upon electrical stimulation.

13. The method according to claim 12 wherein the label is ruthenium (II)-tris-bipyridine.

14. The method according to claim 1 wherein the level of TJ protein in exosomes from the test sample is normalized by dividing it by the level of an exosome marker in the exosomes from the test sample, and the level of TJ protein in the control is normalized by dividing it by the level of an exosome marker in the control.

15. The method according to claim 14 wherein the exosome marker is CD63.

16. A method comprising:
   a) selecting a subject for treatment for an injury to the brain that has progressed on the basis that analysis of the level of a tight junction (TJ) protein in exosomes captured from a first test sample by contacting the sample with antibody to P-glycoprotein relative to the level of said TJ protein in exosomes captured from a second test sample by contacting the sample with antibody to P-glycoprotein, determines that the level of said TJ protein in exosomes captured from said second test sample is elevated relative to the level of said TJ protein in exosomes captured from said first test sample which is an indication that the brain injury has progressed, said first test sample comprising a biological fluid selected from blood, blood plasma, blood serum, cerebrospinal fluid and urine from the subject at a first time point and the second test sample comprising the same biological fluid from the subject at a second time point later relative to the first time point, and said TJ protein selected from the group consisting of occludin, claudin-3, claudin-5, claudin-12, Zonula Occludens-2, Zonula Occludens-3, junctional adhesion molecule-A, junctional adhesion molecule-B, junctional adhesion molecule-C, and any combination thereof, and b) administering to the subject a treatment for an injury to the brain that has progressed.

17. The method of claim 16 wherein said treatment comprises surgical treatment, head elevation, osmotic therapy, hyperventilation, debridement, optimizing venous drainage, cerebrospinal fluid (CSF) drainage, sedation, temperature management, glucose management, administering an antiepileptic drug or administering a neuroprotective agent.

18. The method of claim 17 wherein said CSF drainage comprises the use of a ventricular catheter.

19. The method of claim 17 wherein said optimizing venous drainage comprises keeping the head of the subject in neutral position.

20. The method of claim 17 wherein said osmotic therapy comprises the administration of mannitol or hypertonic saline.

21. The method of claim 17 wherein said sedation comprises the administration of a barbiturate, propofol, a benzodiazepine or an opiate.

22. The method of claim 17 wherein said antiepileptic drug is phenytoin or valproic acid.

23. The method of claim 17 wherein said neuroprotective treatment comprises the administration to the subject of progesterone, magnesium, citicoline, cyclosporine or erythropoietin.

24. The method of claim 17 wherein the TJ protein is selected from the group consisting of occludin, claudin-5, and the combination thereof.

25. The method of claim 16, wherein the level of said TJ protein determined in exosomes from said first test sample is normalized by dividing it by the level of an exosome marker in said first test sample and the level of said TJ protein in exosomes from said second test sample is normalized by dividing it by the level of an exosome marker in said second test sample.

26. The method according to claim 25, wherein the exosome marker is CD63.

* * * * *

SEQUENCE LISTING

<160> NUMBER OF SEQ ID NOS: 2

<210> SEQ ID NO 1
<211> LENGTH: 14
<212> TYPE: PRT

```
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (8)..(8)
<223> OTHER INFORMATION: Serine at position 8 is phosphorylated

<400> SEQUENCE: 1

Lys Gln Leu Lys Ser Lys Leu Ser His Ile Lys Arg Met Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (6)..(6)
<223> OTHER INFORMATION: Threonine at position 6 is phosphorylated

<400> SEQUENCE: 2

Ala Pro Arg Arg Pro Thr Ala Asn Gly Asp Tyr Asp Lys
1               5                   10
```